(12) United States Patent
Riedel et al.

(10) Patent No.: US 10,227,281 B2
(45) Date of Patent: Mar. 12, 2019

(54) PREPARATION OF 2,6- AND 2,7-DISUBSTITUTED ANTHRAQUINONE DERIVATES

(71) Applicant: BASF SE, Ludwigshafen (DE)

(72) Inventors: Dominic Riedel, Lampertheim (DE); Joaquim Henrique Teles, Waldsee (DE); Thomas Wurm, Heidelberg (DE)

(73) Assignee: BASF SE, Ludwigshafen (DE)

( * ) Notice: Subject to any disclaimer, the term of this patent is extended or adjusted under 35 U.S.C. 154(b) by 209 days.

(21) Appl. No.: 15/315,143

(22) PCT Filed: May 28, 2015

(86) PCT No.: PCT/EP2015/061820
§ 371 (c)(1),
(2) Date: Nov. 30, 2016

(87) PCT Pub. No.: WO2015/181283
PCT Pub. Date: Dec. 3, 2015

(65) Prior Publication Data
US 2018/0215694 A1    Aug. 2, 2018

(30) Foreign Application Priority Data

May 30, 2014   (EP) .................................... 14170545

(51) Int. Cl.
| | | |
|---|---|---|
| *C07C 46/08* | (2006.01) | |
| *C07C 37/14* | (2006.01) | |
| *C01B 15/00* | (2006.01) | |
| *C01B 15/023* | (2006.01) | |
| *C07C 46/00* | (2006.01) | |
| *B01D 9/00* | (2006.01) | |
| *B01D 11/04* | (2006.01) | |
| *C07C 50/18* | (2006.01) | |
| *C07C 50/20* | (2006.01) | |

(52) U.S. Cl.
CPC ............... *C07C 46/08* (2013.01); *B01D 9/00* (2013.01); *B01D 11/0492* (2013.01); *C01B 15/023* (2013.01); *C07C 37/14* (2013.01); *C07C 46/00* (2013.01); *C07C 50/18* (2013.01); *C07C 50/20* (2013.01); *C07C 2521/02* (2013.01); *C07C 2521/06* (2013.01); *C07C 2523/04* (2013.01); *C07C 2523/06* (2013.01); *C07C 2523/42* (2013.01); *C07C 2523/44* (2013.01); *C07C 2523/72* (2013.01); *C07C 2603/22* (2017.05); *Y02P 20/582* (2015.11)

(58) Field of Classification Search
CPC ......... C07C 46/08; C07C 37/14; C07C 50/18; C07C 50/20; C01B 15/023
See application file for complete search history.

(56) References Cited

U.S. PATENT DOCUMENTS 6,153,169 A    11/2000   Glenneberg et al.
6,355,815 B1    3/2002   Glenneberg et al.

FOREIGN PATENT DOCUMENTS

| DE | 1 051 257 | 2/1959 |
| DE | 43 39 649 A1 | 5/1995 |
| EP | 1 178 032 A1 | 2/2002 |
| GB | 1 387 511 | 3/1975 |
| GB | 1 387 512 | 3/1975 |
| WO | 99/52819 A1 | 10/1999 |

OTHER PUBLICATIONS

International Search Report and Written Opinion dated Jul. 27, 2015 in PCT/EP2015/061820 filed May 28, 2015.
Gustaaf Goor et al., "Hydrogen Peroxide", Ullmann's Encyclopedia of Industrial Chemistry, 2012, vol. 18, pp. 393-427.

*Primary Examiner* — Sikarl A Witherspoon
(74) *Attorney, Agent, or Firm* — Oblon, McClelland, Maier & Neustadt, L.L.P.

(57) ABSTRACT

A composition comprising a compound of formula (Va) wherein n is 1 or 2 and wherein m is 1 or 2, with n and m preferably both being 1 or both being 2, more preferably both being 1, and/or, preferably and, a compound of formula, wherein n is 1 or 2 and wherein m is 1 or 2, with n and m preferably both being 1 or both being 2, more preferably both being 1, and wherein at least 90 weight-% of the composition consist of compounds of formula (Va) and formula (Vb).

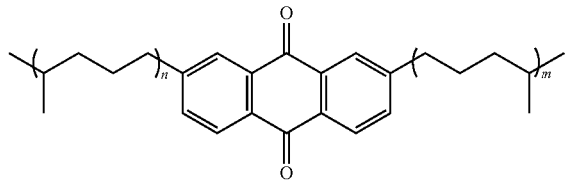

(Va)

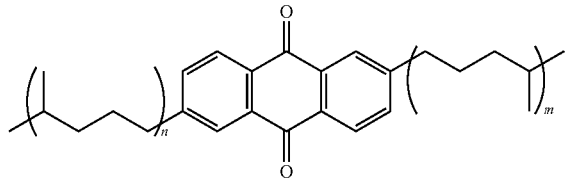

(Vb)

18 Claims, No Drawings

PREPARATION OF 2,6- AND 2,7-DISUBSTITUTED ANTHRAQUINONE DERIVATES

The present invention relates to a process for the preparation of an anthraquinone derivative as well as to an anthraquinone derivative as such and to a mixture and a composition comprising an anthraquinone derivative. Further, the present invention relates to the use of an anthraquinone derivative in a process for the preparation of hydrogen peroxide. Further, the present invention relates to a process for the preparation of hydrogen peroxide using an anthraquinone derivative.

Anthraquinone compounds are suitable for the preparation of hydrogen peroxide. For example, an anthraquinone process is described in Ullmann's Encyclopedia of Industrial Chemistry, Vol. 18, chapter "Hydrogen Peroxide", DOI: 10.1002/14356007.a13_443.pub2. According to chapter 4 of this document, the following criteria must be fulfilled when applying an anthraquinone derivative to the synthesis of hydrogen peroxide: a) good solubility of the quinone form and the hydroquinone form in the solvents used in the process, b) good availability, c) good resistance to oxidation, and d) good resistance to hydrogenation of the aromatic rings in the anthraquinone molecule.

GB 1 387 511 A1 and GB 1 387 512 A1 are directed to a process for the preparation of hydrogen peroxide by use of alkylanthraquinones, wherein the solubility of the dialkylanthraquinones is in the range of from 0.64 mol/l to 0.70 mol/l and 0.65 mol/l to 1.02 mol/l, respectively. Further, GB 1 387 511 A1 and GB 1 387 512 A1 describe general processes for the preparation of the dialkylanthraquinones by condensing a 4-alkyl substituted phthalic anhydride and an alkylbenzene in the presence of a catalyst or by an alkylation reaction followed by oxidation of the obtained anthracene. According to the examples of GB 1 387 511 A1 and GB 1 387 512 A1 only one specific compound, 2-methyl-amylanthraquinone, is used in a process for the preparation of hydrogen peroxide. However, the preparation of 2-methyl-amylanthraquinone is expensive and therefore, highly disadvantageous for industrial-scale processes.

DE 43 39 649 A1 is directed to a process for the preparation of hydrogen peroxide wherein alkylanthraquinones are employed. According to this document, a mixture of 1,3-diethylanthraquinone, 2,3-diethylanthraquinone, 1,4-diethylanthraquinone, 1,2,3-triethylanthraquinone and 2-ethylanthraquinone is used for increasing the solubility of the anthraquinone derivatives in the solvent used in the process for the preparation of hydrogen peroxide.

DE 1 051 257 B is directed to a process for the preparation of hydrogen peroxide via an anthraquinone process, wherein anthraquinone derivatives having two or three alkyl residues are used. According to DE 1 051 257 B, it is preferred to use a mixture of isomers of the anthraquinone derivatives.

In the prior art several anthraquinone derivatives are disclosed for use in a process for the preparation of the hydrogen peroxide. However, the disclosed anthraquinone derivatives are either expansive to prepare and/or not sufficiently soluble in the solvents which are commonly used for the preparation of hydrogen peroxide and/or not sufficiently stable towards hydrogenation of the aromatic ring systems, leading to products that are not active with respect to hydrogen peroxide synthesis anymore.

It was an object of the present invention to provide an advantageous process for the preparation of an anthraquinone derivative. Further, it was an object of the present invention to provide a novel anthraquinone derivative which has a better suitability than known anthraquinone derivatives when used in a process for the preparation of hydrogen peroxide, including a higher stability towards over-hydrogenation reactions.

Surprisingly, it was found that a process starting from a compound of formula (I)

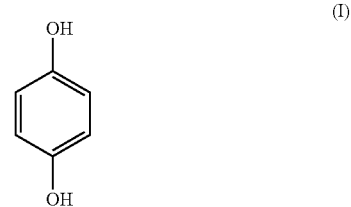

allows for the preparation of an anthraquinone derivative in an effective manner. For example, according to a possible embodiment, the process can be carried out as a one-pot synthesis. Further, it was surprisingly found that the anthraquinone derivatives according to the present invention exhibit a high solubility in a solvent especially suitable for use in a process for the preparation of hydrogen peroxide.

Therefore, the present invention relates to a process for the preparation of an anthraquinone derivative comprising
(i) providing a mixture (A) comprising a compound of formula (I)

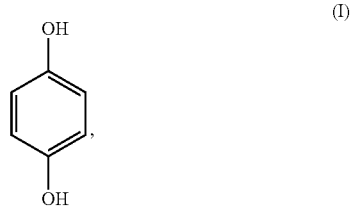

a compound of formula (II)

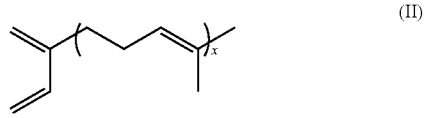

wherein x is 1, or a compound of formula (II) wherein x is 2, or a mixture of a compound of formula (II) wherein x is 1 and a compound of formula (II) wherein x is 2, a dehydrogenation catalyst, and a liquid solvent system;

(ii) treating the mixture (A) with an oxygen-containing gas obtaining a mixture (B) comprising a compound of formula (IIIa)

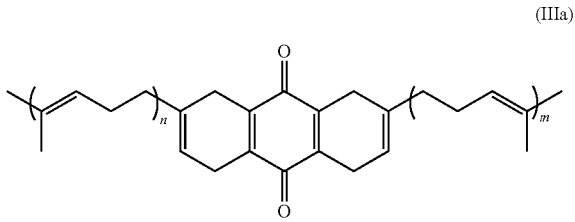

and/or, preferably and, a compound of formula (IIIb)

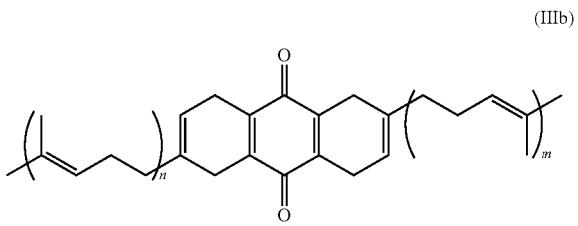

wherein n is 1 or 2 and wherein m is 1 or 2;
(iii) treating the mixture (B), optionally after work-up, with an oxygen-containing gas, obtaining a mixture (C) comprising a compound of formula (IVa)

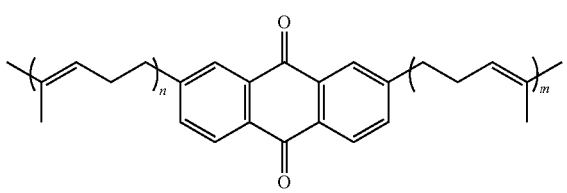

and/or, preferably and, a compound of formula (IVb)

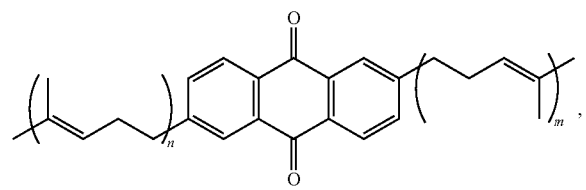

wherein n is 1 or 2 and wherein m is 1 or 2.

If the mixture (A) provided in (i) comprises a compound of formula (II) wherein x is 1, the mixture (B) obtained in (ii) comprises a compound of formula (IIIa) and/or, preferably and, a compound of formula (IIIb) wherein n is 1 and m is 1, and the mixture (C) obtained in (iii) comprises a compound of formula (IVa) and/or, preferably and, a compound of formula (IVb) wherein n is 1 and m is 1. If the mixture (A) provided in (i) comprises a compound of formula (II) wherein x is 2, the mixture (B) obtained in (ii) comprises a compound of formula (IIIa) and/or, preferably and, a compound of formula (IIIb) wherein n is 2 and m is 2, and the mixture (C) obtained in (iii) comprises a compound of formula (IVa) and/or, preferably and, a compound of formula (IVb) wherein n is 2 and m is 2. If the mixture (A) provided in (i) comprises a mixture of a compound of formula (II) wherein x is 1 and a compound of formula (II) wherein x is 2, the mixture (B) obtained in (ii) comprises a compound of formula (IIIa) and/or, preferably and, a compound of formula (IIIb) wherein n is 1 and m is 2, and the mixture (C) obtained in (iii) comprises a compound of formula (IVa) and/or, preferably and, a compound of formula (IVb) wherein n is 1 and m is 2.

According to a preferred first alternative of the present invention, the mixture (A) provided in (i) comprises a compound of formula (II) wherein x is 1, the mixture (B) obtained in (ii) comprises a compound of formula (IIIa) and/or, in particular and, a compound of formula (IIIb) wherein n is 1 and m is 1, and the mixture (C) obtained in (iii) comprises a compound of formula (IVa) and/or, in particular and, a compound of formula (IVb) wherein n is 1 and m is 1.

According to a preferred second alternative of the present invention, the mixture (A) provided in (i) comprises a compound of formula (II) wherein x is 2, the mixture (B) obtained in (ii) comprises a compound of formula (IIIa) and/or, in particular and, a compound of formula (IIIb) wherein n is 2 and m is 2, and the mixture (C) obtained in (iii) comprises a compound of formula (IVa) and/or, in particular and, a compound of formula (IVb) wherein n is 2 and m is 2.

Step (i)

Generally, no specific restrictions exist regarding the nature of the dehydrogenation catalyst provided that a mixture (B) comprising a compound of formula (IIIa) and/or, preferably and, a compound of formula (IIIb) is obtained in (ii). Preferably, the dehydrogenation catalyst according to (i) comprises at least on element selected from the group of transition metals and a combination of two or more thereof, wherein the dehydrogenation catalyst more preferably comprises copper and at least one additional element selected from the group consisting of lithium, zinc, zirconium, aluminum, and a combination of two or more thereof, wherein the dehydrogenation catalyst more preferably comprises a combination of copper, and lithium or a combination of copper, zinc, zirconium and aluminum. More preferably, the dehydrogenation catalyst comprises, more preferably consists of, a combination of lithium chloride and copper(II) chloride, or of a combination of copper(II) oxide, zinc(II) oxide, zirconium(IV) oxide and aluminum oxide.

Generally, there are no specific restrictions how the dehydrogenation catalyst is employed in (ii) provided that the dehydrogenation catalyst is able to catalyze the reaction according to (ii). Preferably, the dehydrogenation catalyst is employed suspended or dissolved in the liquid solvent system. If the dehydrogenation catalyst comprises, preferably consists of a combination of lithium chloride and copper(II) chloride, it is particularly preferred that the dehydrogenation catalyst is at least partially, more preferably completely, dissolved in the liquid solvent system. If the dehydrogenation catalyst comprises, preferably consists of a combination of copper(II) oxide, zinc(II) oxide, zirconium (IV) oxide and aluminum oxide, it is particularly preferred that the dehydrogenation catalyst is at least partially, more preferably completely, dispersed in the liquid solvent system.

As far as the amounts of the compound of formula (I) and of the compound of formula (II) are concerned present in the mixture (A) according to (i), no specific restrictions exist. Preferably, for providing the mixture (A), the compound of formula (I) is admixed with the compound of formula (II) at a molar ratio of the compound of formula (I) relative to the compound of formula (II) in the range of from 0.1:1 to 0.5:1, preferably from 0.2:1 to 0.5:1, more preferably from 0.4:1 to 0.5:1.

As far as the liquid solvent system according to (i) is concerned, no specific restrictions exist. Preferably, the liquid solvent system according to (i) comprises an organic solvent, preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof.

It is preferred that the liquid solvent system according to (i) further comprises water. Thus, it is preferred that the liquid solvent system according to (i) comprises an organic solvent, preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof.

Concerning the molar ratio of organic solvent relative to water in the liquid solvent system according to (i), no specific restrictions exist. Preferably, the mixture (A) according to (i) comprises the organic solvent and the water at a molar ratio of organic solvent relative to water in the range of from 1:1 to 5:1, preferably from 1.2:1 to 3.5:1, more preferably from 1.3:1 to 3:1, more preferably from 1.4:1 to 2.75:1, more preferably from 1.5:1 to 2.5:1, more preferably from 1.6:1 to 2.4:1, more preferably from 1.7:1 to 2.3:1, more preferably from 1.75:1 to 2.25:1. In this context, the term "organic solvent" relates to all organic solvents contained in the liquid solvent system if more than one different organic solvent are contained in the liquid solvent system.

Further, the liquid solvent system according to (i) may not comprise water. In this case, it is preferred that the liquid solvent system according to (i) consists of an organic solvent preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof.

Concerning the temperature of the mixture provided in (i) no specific restrictions exist. It is preferred that prior to (ii), the mixture (A) is heated to a temperature in the range of from 40 to 150° C., preferably from 45 to 120° C., more preferably from 50 to 100° C. such as from 55 to 75° C.

Regarding the sequence of admixing the compounds for providing the mixture (A), no specific restrictions exist. Preferably, the dehydrogenation catalyst is admixed with the liquid solvent system first, and the compounds of formula (I) and (II) are added to the resulting mixture of dehydrogenation catalyst and liquid solvent system. During mixing, the mixture can be suitably agitated, for example stirred.

Therefore, step (i) of the process of the present invention preferably comprises
(i.1) preparing a mixture (A.1) comprising at least a portion of the dehydrogenation catalyst and at least a portion of the liquid solvent system;
(i.2) adding at least a portion of the compound of formula (I) and at least a portion of the compound of formula (II) to the mixture (A.1) prepared in (i.1), obtaining at least a portion of the mixture (A).

Further preferably, step (i) of the process of the present invention preferably comprises
(i.1) preparing a mixture (A.1) comprising the dehydrogenation catalyst and the liquid solvent system;
(i.2) adding the compound of formula (I) and the compound of formula (II) to the mixture (A.1) prepared in (i.1), obtaining the mixture (A).

Regarding (i.2), the compound of formula (I) and the compound of formula (II) can be added to (A.1) either simultaneously or sequentially, wherein, if they are added sequentially, it is possible, for example, to add the compound of formula (I) first and then add the compound of formula (II), or to add the compound of formula (I) first and then add the compound of formula (I).

Step (ii)

Concerning treating the mixture (A) with an oxygen-containing gas according to (ii), no specific restrictions exist concerning the period of time during which the mixture is treated with the oxygen-containing gas. Preferably, in (ii), the mixture (A) is treated with the oxygen-containing gas for a period of time in the range of from 0.1 to 240 h, preferably from 0.2 to 200 h, more preferably from 0.5 to 160 h, more preferably from 0.6 to 120 h, more preferably from 0.75 to 100 h, more preferably from 1 to 90 h.

No specific restrictions how the mixture (A) is treated with the oxygen-containing gas provided that a mixture (B) comprising a compound of formula (IIIa) and a compound of formula (IIIb) is obtained. It is particularly preferred that the oxygen-containing gas is passed through the mixture (A). During the treatment, the mixture (A) can be suitably agitated, for example stirred.

Therefore, it is preferred that in (ii), the mixture (A) is treated with the oxygen-containing gas for a period of time in the range of from 0.1 to 240 h, preferably from 0.5 to 160 h, more preferably from 1 to 90 h, preferably by passing the oxygen-containing gas through the mixture (A).

As far as the oxygen-containing gas according to (ii) is concerned, no specific restrictions exist provided that a mixture (B) comprising a compound of formula (IIIa) and a compound of formula (IIIb) is obtained. Preferably, the oxygen-containing gas according to (ii) is selected from the group consisting of oxygen, air, and lean air. Mixtures of two or three thereof can be employed.

Preferably, the mixture (B) obtained in (ii) comprises an organic solvent and water. In this case, it is preferred that prior to (iii) the mixture (B) obtained in (ii) is subjected to a work-up step which preferably comprises separating at least a portion of the water contained in (B) from the mixture (B). More preferably, the work-up comprises separating at least 70 weight-%, more preferably at least 80 weight-%, more preferably at least 90 weight-%, more preferably at least 95 weight-%, more preferably at least 98 weight-% of the water contained in (B) from (B). All suitable methods for separating the water can be used, for example extraction, distillation or drying by using a suitable drying agent. Preferably, the water is separated from (B) by extraction or distillation Thus, it is preferred that the mixture (B) comprises water and is treated with the oxygen-containing gas after work-up, the work-up comprising separating at least a portion of the water from the mixture (B).

It is preferred that prior to the work-up, the mixture (B) is cooled to a temperature in the range of from 10 to 35° C., preferably from 15 to 30° C., more preferably from 18 to 27° C., more preferably from 20 to 25° C.

Further, the mixture (B) obtained in (ii) may contain a dimer of the compound of formula (II), wherein the dimer may be formed by a Diels-Alder reaction of two molecules of the formula (II). Whether or not such a dimer is contained in (B) can be determined by all suitable experimental methods, for example by GC/MS, NMR, IR and/or HPLC. If such a dimer is contained in (B), the dimer is preferably suitably separated from the mixture (B), for example by crystallization, filtration, centrifugation, extraction and/or distillation. Preferably, the thus separated dimer is subjected to a retro-Diels-Alder reaction under suitably conditions, preferably including temperatures between 80 and 250° C., from which retro-Diels-Alder reaction the compound of formula (II) is obtained which is preferably re-used as starting material for the preparation of the mixture (A) according to (i).

Therefore, it is possible that the work-up further comprises
(ii.1) separating the dimer of the compound of formula (II) from the mixture (B) obtained in (ii),
(ii.2) subjecting the separated dimer of the compound of formula (II) to a retro-Diels-Alder reaction, obtaining the compound of formula (II);
(ii.3) recycling the compound of formula (II) obtained from (i.b) to (i).

Thus, the process of the present invention preferably comprises, according to (iii), the treating of the mixture (B), after work-up, with an oxygen-containing gas, wherein said work-up preferably comprises either separating at least a portion of the water contained in (B) from (B), or separating the dimer of the compound of formula (II) from (B), or both separating at least a portion of the water contained in (B) from (B) and separating the dimer of the compound of formula (II) from (B).

If the work-up comprises both separating at least a portion of the water contained in (B) from (B) and separating the dimer of the compound of formula (II) from (B), it is preferred that in a first step, the at least 70% of the water is separated, and in a second step, the dimer is separated by one of the suitable methods mentioned above.

According to a conceivable embodiment, the mixture (B) obtained in (ii) does not comprise water and the liquid solvent system consists of an organic solvent. Further, it is conceivable that the mixture (B) obtained in (i) either does not contain the dimer of the compound of formula (II), or is not subjected, prior to (iii), to the separation of the dimer. In this case, it is preferred that the mixture (B) is subjected to the treatment with an oxygen-containing gas according to (iii) without any work-up of this mixture, i.e. the mixture (B) as obtained from (ii) is directly subjected to the treatment with an oxygen-containing gas according to (iii). Therefore, the sequence of steps (i) to (iii) is preferably carried out as a one-pot process, and the present invention also relates to the process as described above comprising
(i) providing a mixture (A) comprising a compound of formula (I)

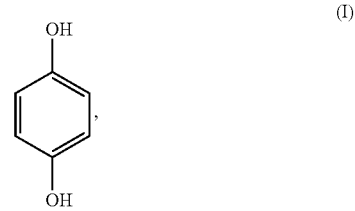

a compound of formula (II)

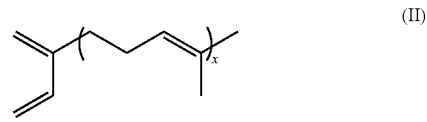

wherein x is 1, or a compound of formula (II) wherein x is 2, or a mixture of a compound of formula (II) wherein x is 1 and a compound of formula (II) wherein x is 2, a dehydrogenation catalyst, and a liquid solvent system;
(ii) treating the mixture (A) with an oxygen-containing gas obtaining a mixture (B) comprising a compound of formula (IIIa)

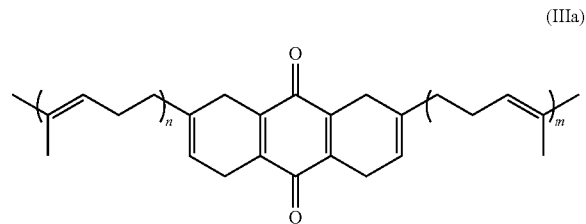

and/or, preferably and, a compound of formula (IIIb)

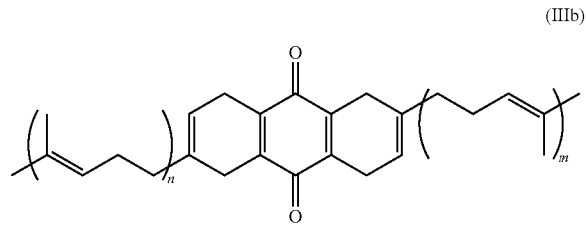

wherein n is 1 or 2 and wherein m is 1 or 2;

(iii) directly treating the mixture (B) as obtained from (ii), without any further work-up, with an oxygen-containing gas, obtaining a mixture (C) comprising a compound of formula (IVa)

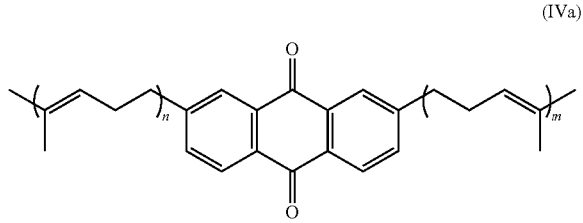

(IVa)

and/or, preferably and, a compound of formula (IVb)

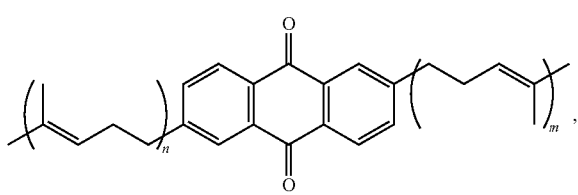

(IVb)

wherein n is 1 or 2 and wherein m is 1 or 2.

Step (iii)

Concerning treating the mixture (B) with an oxygen-containing gas according to (iii), no specific restrictions exist concerning the period of time during which the mixture is treated with the oxygen-containing gas. Preferably, in (iii), the mixture (B) is treated with the oxygen-containing gas for a period of time in the range of from 0.1 to 150 h, preferably from 0.2 to 120 h, more preferably from 0.5 to 120 h, more preferably from 0.6 to 110 h, more preferably from 0.75 to 100 h, more preferably from 1 to 90 h.

No specific restrictions exist how the mixture (B) is treated with the oxygen-containing gas provided that a mixture (C) comprising a compound of formula (IVa) and/or, preferably and, a compound of formula (IVb) is obtained. It is particularly preferred that the oxygen-containing gas is passed through the mixture (B).

During the treatment, the mixture (B) can be suitably agitated, for example stirred.

Therefore, it is preferred that in (iii), the mixture (B) is treated with the oxygen-containing gas for a period of time in the range of from 0.1 to 150 h, preferably from 0.5 to 120 h, more preferably from 1 to 90 h, preferably by passing the oxygen-containing gas through the mixture (B).

As far as the oxygen-containing gas according to (iii) is concerned, no specific restrictions exist provided that a mixture (C) comprising a compound of formula (IVa) and a compound of formula (IVb) is obtained. Preferably, the oxygen-containing gas according to (iii) is selected from the group consisting of oxygen, air, and lean air. A mixture of two or three thereof can be employed.

Further, it is preferred that the mixture (B) treated in (iii) comprises an inorganic base. Concerning the nature of the inorganic base, no specific restrictions exist provided that a mixture (C) comprising a compound of formula (IVa) and/or, preferably and, a compound of formula (IVb) is obtained. Preferred inorganic bases include, but are not restricted to, alkali metal bases and alkaline earth metal bases, preferably hydroxides, more preferably alkali metal bases, more preferably alkali metal hydroxides, more preferably potassium and/or sodium hydroxides. Thus, the treating in (iii) is preferably carried out in the presence of an inorganic base, preferably selected from the group consisting potassium hydroxide, sodium hydroxide, and a combination thereof. According to the present invention, it is particularly preferred that the inorganic base is potassium hydroxide.

Preferably, the inorganic base is employed at a molar ratio of the inorganic base relative to compound of formula (I) in the range of from 0.01:1 to 1:1, preferably from 0.1:1 to 1:1, more preferably from 0.2:1 to 1:1.

As far as the temperature at which the treating in (iii) is carried out is concerned, no specific restrictions exist provided that a mixture comprising the compound of formula (IVa) and/or, preferably and, the compound of formula (IVb) is obtained. Preferably, the temperature at the beginning of the treating in (iii) is the range of from 30 to 150° C., preferably from 40 to 100° C., more preferably from 50 to 90° C., more preferably from 55 to 80° C.

Step (iv)

Generally, the mixture (C) obtained from (iii) may be used as such for all suitable purposes, for example as mixture comprising one or more anthraquinone compounds for the preparation of hydrogen peroxide. Preferably, the mixture (C) obtained from (iii) is first subjected to at least one further step, preferably including a separation step (iv) in according to which the one or more anthraquinone compounds contained in the mixture (C) obtained from (iii) are at least partially, preferably essentially completely separated.

Therefore, it is preferred that the process according to the present invention further comprises (iv) separating the compound of formula (IVa) and/or, preferably and, the compound of formula (IVb) from the mixture (C), obtaining a mixture of which at least 90 weight-%, preferably at least 92 weight-%, more preferably at least 94 weight-%, more preferably at least 96 weight-% such as at least 99 weight-% consist of the compound of formula (IVa) and/or, preferably and, the compound of formula (IVb).

As regards the separation according to (iv), all methods of separating the compound of formula (IVa) and/or, preferably and, the compound of formula (IVb) from the mixture (C) are conceivable. These methods include, but are not restricted to, distillation methods, crystallization methods and extraction methods. Preferably, the compound of formula (IVa) and/or, preferably and, the compound of formula (IVb) are separated by a method comprising extracting the organic phase, preferably extracting the organic phase with water, preferably to remove at least partially, more preferably essentially completely, the inorganic base which is preferably comprised in the mixture (B) treated in (iii).

After the extraction of the organic phase, which is preferably carried out with water, the organic phase containing the compound of formula (IVa) and/or, preferably and, the compound of formula (IVb) is optionally subjected to a suitable drying step wherein, preferably, the organic solvent is at least partially, more preferably essentially completely removed and a solid is obtained comprising, preferably essentially consisting of, the compound of formula (IVa) and/or, preferably and, the compound of formula (IVb). No specific restrictions exist regarding the drying step. Preferably, the drying includes the drying of the organic phase in the presence of a drying agent such as a molecular sieve, an alkali metal or alkaline earth metal salts, preferably selected from the group consisting of magnesium sulfate, sodium sulfate, and a combination thereof, preferably sodium sulfate, or the like, preferably followed by an evaporation treatment, preferably under reduced pressure wherein, from the evaporation treatment, a solid is preferably obtained which comprises, preferably essentially consists of, the compound of formula (IVa) and/or, preferably and, the compound of formula (IVb).

If said drying is carried out, it is preferred that the solid obtained from the drying is dissolved in a suitable organic solvent preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof, more preferably selected from the group consisting of alcohols, having 1 to 12 carbon atoms. Preferably, the dissolving is carried out at a temperature higher than ambient temperature, preferably in the range of from 50 to 250° C., more preferably from 60 to 150° C.

If said drying is not carried out, it is preferred that the organic phase obtained from extraction is admixed with a suitable organic solvent preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof, more preferably selected from the group consisting of alcohols, having 1 to 12 carbon atoms. Preferably, the admixing is carried out at a temperature higher than ambient temperature, preferably in the range of from 50 to 250° C., more preferably from 60 to 150° C.

Preferably, the solution obtained from said dissolving or from said admixing, having a temperature preferably in the range of from 50 to 250° C., more preferably from 60 to 150° C., is suitably cooled wherein from said cooling, a suspension is obtained comprising, preferably essentially consisting of, the compound of formula (IVa) and/or, preferably and, the compound of formula (IVb). Preferably, the solution is cooled from a temperature in the range of from 50 to 250° C., preferably from 60 to 150° C., to a temperature in the range of from −30 to +25° C., more preferably from −25 to +5° C., obtaining said suspension.

Preferably, the solid contained in said suspension obtained from cooling is then separated from the respective liquid. Preferably, said separating includes a filtration or a centrifugation step which is preferably followed by one or more suitable washing steps. If washing is carried out, it is preferred that the temperature of the one or more washing agents is in the range of from −30 to +25° C., more preferably from −25 to +5° C. As washing agents, an organic solvent is preferably used described above in the context of the dissolving or the admixing, i.e. an organic solvent preferably selected from the group selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof, more preferably selected from the group consisting of alcohols having 1 to 12 carbon atoms. According to an embodiment of the present invention, the organic solvent used for said dissolving or said admixing is the same solvent which is used as washing agent.

Preferably, after the separation preferably comprising filtration or centrifugation or distillation, more preferably comprising filtration or centrifugation or distilling, and washing, the separated solid is subjected to a suitable drying step. No specific restrictions exist regarding the drying step. Preferably, the drying includes an evaporation treatment, preferably under reduced pressure wherein, from the evaporation treatment, a solid is preferably obtained which comprises, preferably essentially consists of, the compound of formula (IVa) and/or, preferably and, the compound of formula (IVb). Preferred reduced pressures are in the range of from 1 to 950 mbar, more preferably from 1 to 800 mbar.

Further, it is possible that the thus dried solid is further purified by any suitable method such as crystallization methods and chromatography methods like chromatography on silica using a suitable eluent such as cyclohexane or ethyl acetate or a combination thereof, wherein chromatography methods are preferred.

Therefore, the present invention also relates to the process as described above wherein the separation according to (iv) comprises (iv.1) extracting the mixture (C), preferably with water;
(iv.2) optionally evaporating the organic solvent, preferably under reduced pressure after extracting the organic phase obtained from (iv.1), preferably with water obtaining a solid,
(iv.3) dissolving the solid obtained from (iv.2), preferably at a temperature in the range of from 50 to 250° C., more preferably from 60 to 200° C., wherein the organic solvent is preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N- dialkyl carbamates, N-alkyl carbonamides, tetraalkyl ureas, cycloalkyl ureas, and a mixture of two or more thereof, more preferably selected from the group consisting of alcohols, having 1 to 12 carbon atoms;
(iv.4) cooling the solution obtained from (iv.3), preferably to temperature in the range of from −30 to +25° C., more preferably from −25 to +5° C., obtaining a suspension;
(iv.5) separating the solid from the suspension obtained from (iv.4);
(iv.6) preferably drying the solid obtained from (iv.5), preferably under vacuum;
(iv.7) optionally further purifying the solid obtained from (iv.5) or from (iv.6), preferably from (iv.6), preferably by chromatography.

According to the present invention, it is generally possible to use the mixture obtained from (iv.1) and preferably subject this mixture to the step (v) as described below wherein according to this embodiment, the steps (iv.2) to (iv.7) are not carried out. According to the present invention, it is also possible to use the mixture obtained from (iv.5), preferably from (iv.6), optionally from (iv.7), and preferably subject this mixture to the step (v) as described below.

Step (v)

Generally, the mixture obtained from (iii) or the solid obtained from (iv), preferably the solid obtained from (iv), can be employed in any conceivable process, for example in a process for the preparation of hydrogen peroxide. Preferably, the mixture obtained from (iii) or the solid obtained from (iv), preferably the solid obtained from (iv), is subjected to a further step according to which the double bonds of the alkyl residues of the compound of formula (IVa) and/or, preferably and, the compound of formula (IVb) are selectively hydrogenated Therefore, the present invention also relates to the process as described above, further comprising
(v) subjecting the mixture obtained in (iii), preferably the mixture obtained in (iv), more preferably the solid obtained in (iv), to a hydrogenation reaction, preferably in a solvent, in the presence of a hydrogenation catalyst, obtaining a mixture comprising a compound of formula (Va)

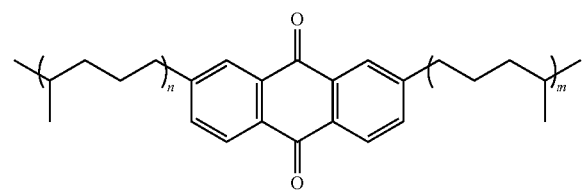

(Va)

and/or, preferably and, a compound of formula (Vb)

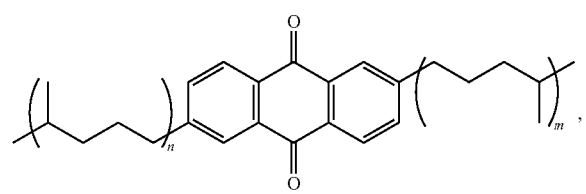

(Vb)

wherein n is 1 or 2 and wherein m is 1 or 2, with n and m preferably both being 1 or both being 2.

It is preferred to carry out the hydrogenation reaction according to (v) in the presence of a solvent. As far as the solvent according to (v) is concerned, no specific restrictions exist provided that a mixture comprising a compound of formula (Va) and/or, preferably and, a compound of formula (Vb) wherein n is 1 or 2 and wherein m is 1 or 2, with n and m preferably both being 1 or both being 2 is obtained. Preferably, the solvent is an organic solvent preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof.

As far as the hydrogenation catalyst according to (v) is concerned, no specific restrictions exist regarding the nature of the hydrogenation catalyst provided the hydrogenation catalyst is able to catalyze the hydrogenation reaction according to (v). Preferably, the hydrogenation catalyst according to (v) comprises one or more metals active in hydrogenation, wherein more preferably, the one or more metals are selected from the group consisting of at least on element selected from the group of transition metals and a combination of two or more thereof, wherein the hydrogenation catalyst more preferably comprises Pd, Rh, Ru, Ni, Re, Os, Ir, Pt, Au, Ag, and a combination of two or more thereof, more preferably Pd, Rh, Ru, Ni, and a combination of two or more thereof, wherein more preferably, the one or more metals comprise Pd, even more preferably consists of Pd Further, it is preferred that one or more metals comprised in the hydrogenation catalyst according to (II) is supported on a support. As regards this support, no specific restrictions exist concerning the nature of the support provided that the hydrogenation catalyst is able to catalyze the hydrogenation reaction according to (III). Preferably, the support comprises at least on element selected from the group consisting of aluminum, barium, calcium, cerium, zirconium, titanium and silicon. More preferably the support comprises at least one compound selected from the group consisting of aluminum oxide, barium sulfate, calcium carbonate, cerium (IV) oxide, silicon oxide and zirconium(IV) oxide, more preferably from the group consisting of aluminum oxide, silicon oxide, and a combination of two or more thereof.

Further, it is preferred that the hydrogenation catalyst use in (v) comprises a ligand. Generally, there are no specific restrictions regarding the nature of the ligand, provided that the hydrogenation catalyst comprising the ligand is able to catalyze the hydrogenation reaction according to (v). Thus, the ligand may be charged or uncharged. Preferably, the ligand is selected from the group consisting of 1,5-cyclooctadiene (COD), tricyclohexylphosphin PCy$_3$), 1,2-Bis(di-tert-butyl-phosphinomethyl)benzol (DTBPP), tetrafluoroborate, chloride, n-tributylphosphine, triethylphospine, methallyl, triphos, and a combination of two or more thereof, more preferably, the ligand is selected from the group consisting of 1,5-cyclooctadiene (COD), tricyclohexylphosphin PCy$_3$), 1,2-Bis(ditert-butyl-phosphinomethyl)benzol (DTBPP), tetrafluoroborate, chloride, and a combination of two or more thereof. Preferably, the hydrogenation reaction according to (ii) is carried out in the presence of a hydrogenation catalyst and in the presence of an additive, wherein the additive is preferably 1-butyl-3-methylimidazolium chloride (BMIMCl). In case the hydrogenation catalyst comprises Rh, 1,5-cyclooctadiene and tetrafluoroborate, it is particularly preferred to carry out the hydrogenation catalyst in the presence of 1-butyl-3-methylimidazolium chloride (BMIMCl).

As far as the temperature at which the hydrogenation reaction according to (v) is carried out is concerned, no specific restrictions exist provided that the selective hydrogenation is achieved. Preferably, the hydrogenation reaction according to (v) is carried out at a temperature in the range of from 20 to 200° C., preferably from 25 to 150° C., more preferably from 30 to 100° C., such as from 30 to 70° C. or from 40 to 80° C. or from 50 to 90° C. or from 60 to 100° C.

As far as the pressure at which the hydrogenation reaction according to (v) is carried out is concerned, no specific restrictions exist provided that the selective hydrogenation is achieved. Preferably, the hydrogenation reaction according to (v) is carried out at a hydrogen pressure in the range of from 1 to 50 bar, preferably from 1 to 30 bar, more preferably from 1 to 20 bar, more preferably from 1 to 10 bar, such as from 1 to 3 bar or from 2 to 7 bar or from 3 to 10 bar.

Preferably, if the hydrogenation reaction according to (v) is carried out at a pressure of 20.0 bar, a temperature of 40° C., for a period of time of 15 h, wherein toluene is used as solvent, the catalyst is not [Ru(PnBu$_3$)$_4$(H$_2$)] [triphos] and/or [Ru(COD)(methallyl)$_2$] [PEt$_3$], preferably not [Ru(PnBu$_3$)$_4$(H$_2$)] and/or [Ru(COD)(methallyl)$_2$], more preferably, the catalyst does not comprise a ligand selected from the group consisting of n-tributylphosphine, triethylphosphine, methallyl, triphos, and a combination of two or more thereof.

As intermediates during the hydrogenation reaction according to (v), the following intermediates and mixtures of two or more intermediates can be obtained, depending on the specific values of the indices n and m of the compound or compounds of formula (IIIa) and/or (IIIb) and, therefore, the value of the index x of the compound or the compounds of formula (II):

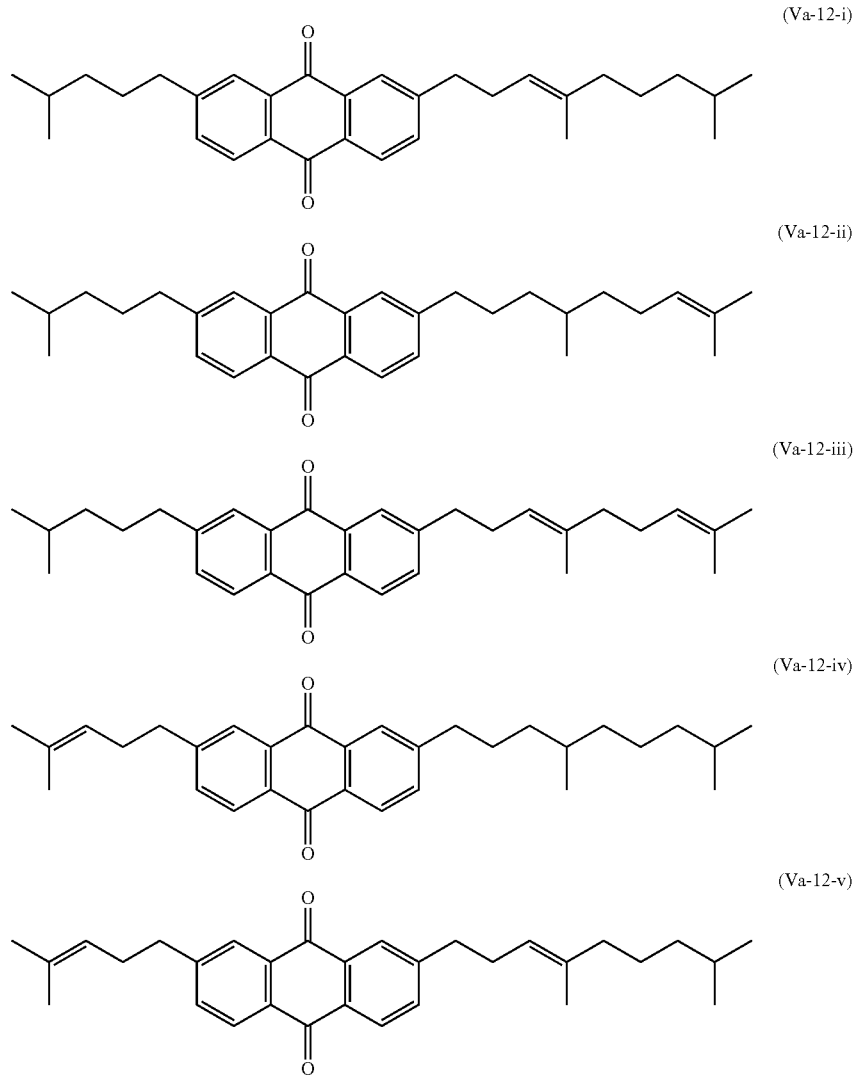

-continued
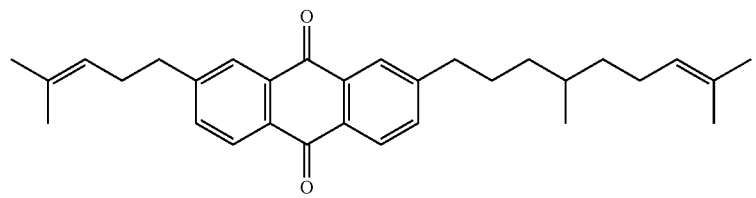
(Va-12-vi)
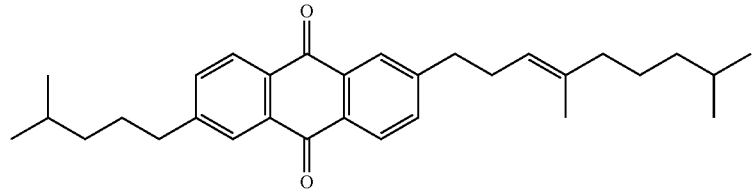
(Vb-12-i)
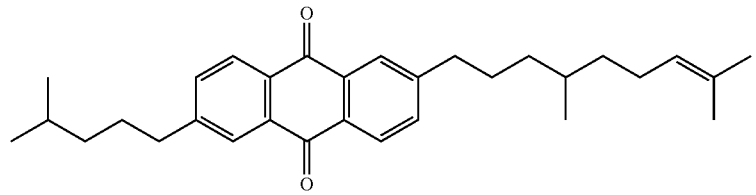
(Vb-12-ii)
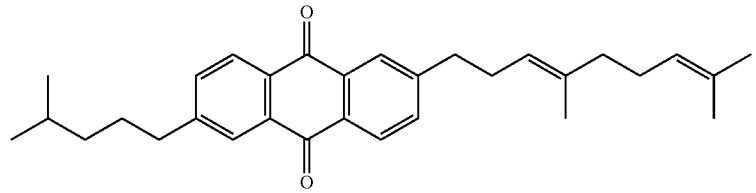
(Vb-12-iii)
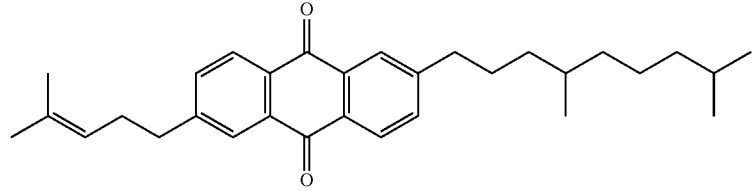
(Vb-12-iv)
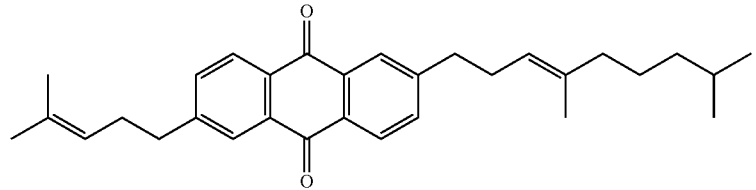
(Vb-12-v)
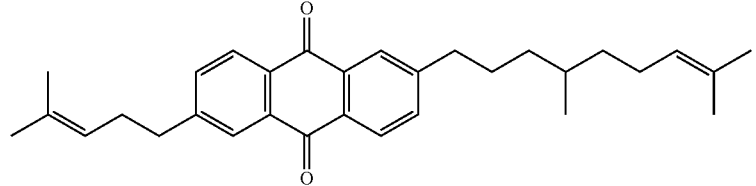
(Vb-12-vi)
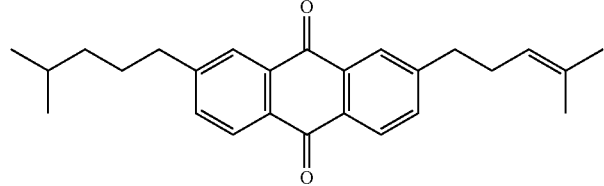
(Va-11-i)

-continued
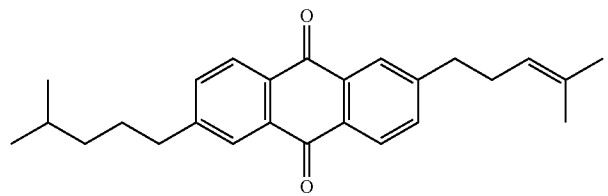
(Vb-11-i)
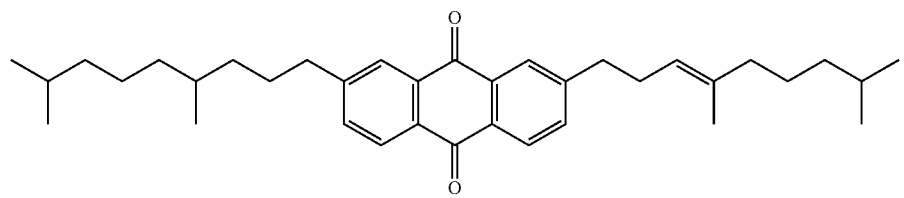
(Va-22-i)
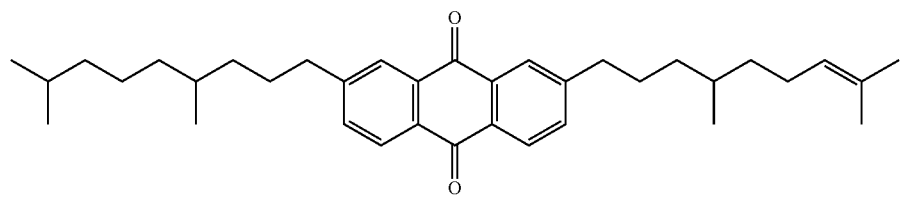
(Va-22-ii)
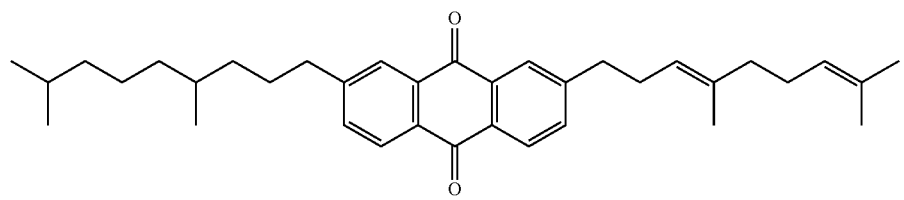
(Va-22-iii)
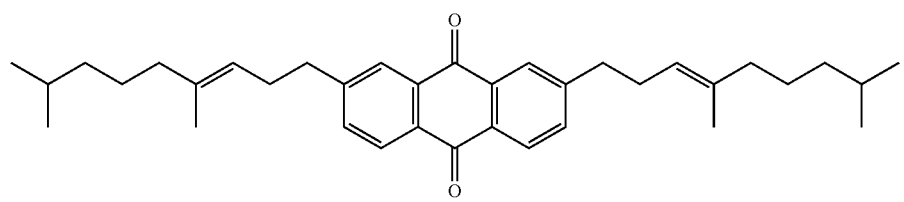
(Va-22-iv)
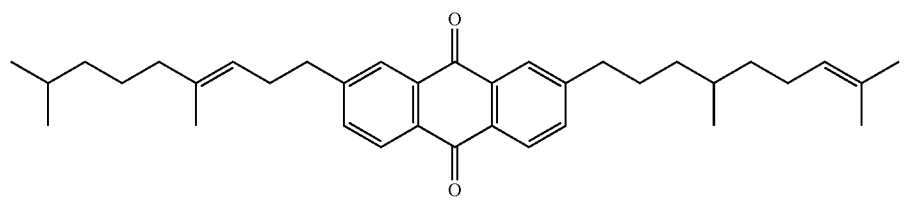
(Va-22-v)
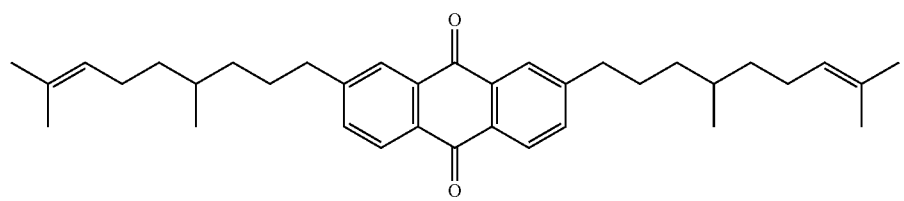
(Va-22-vi)
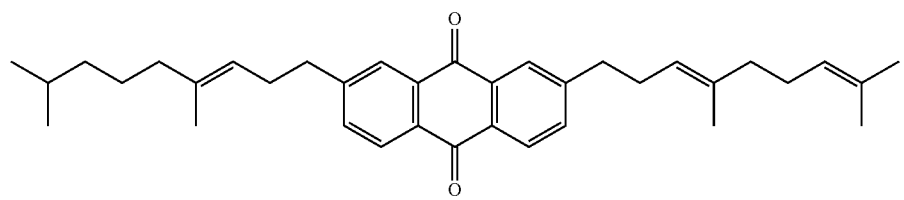
(Va-22-vii)

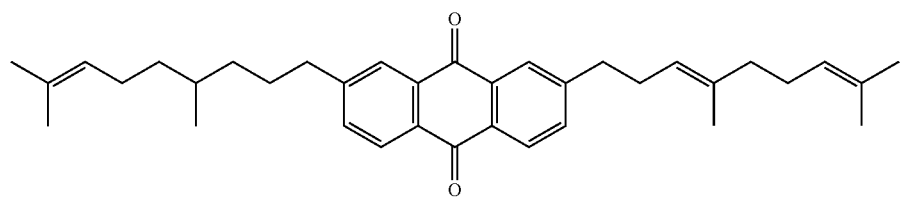
(Va-22-viii)
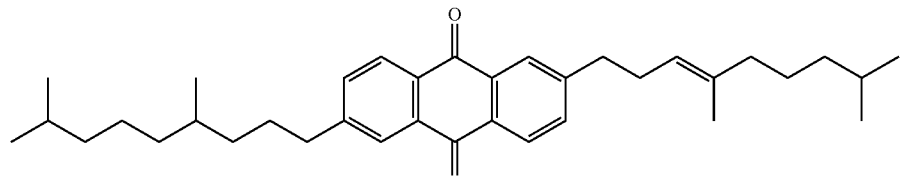
(Vb-22-i)
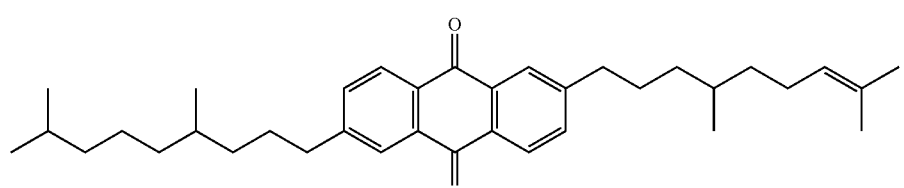
(Vb-22-ii)
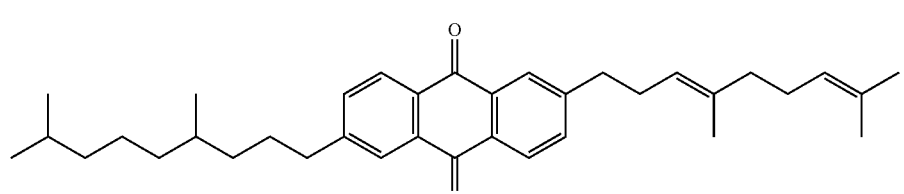
(Vb-22-iii)
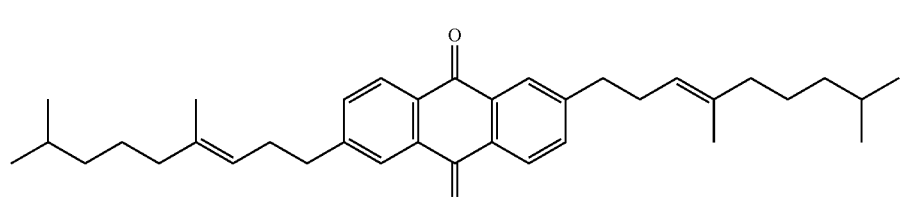
(Vb-22-iv)
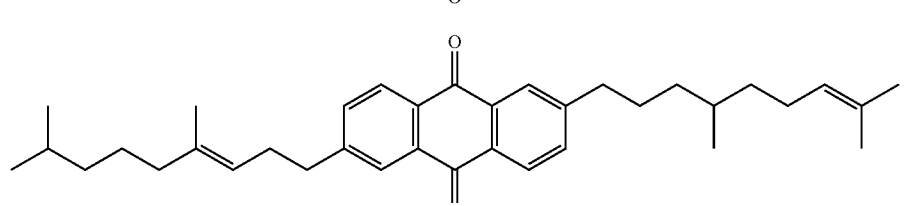
(Vb-22-v)
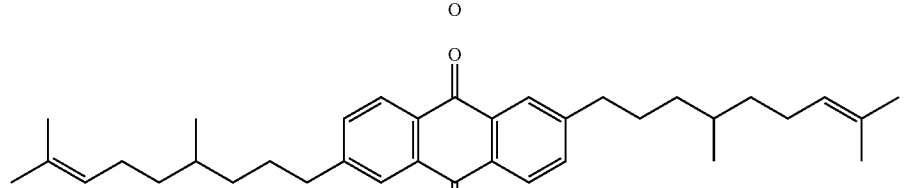
(Vb-22-vi)
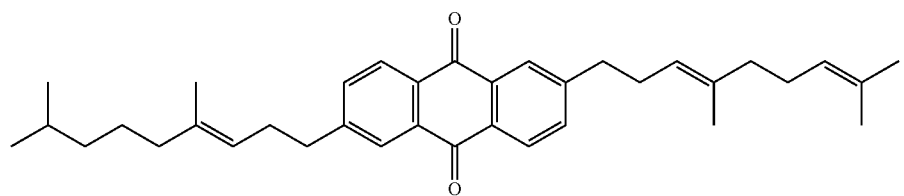
(Vb-22-vii)

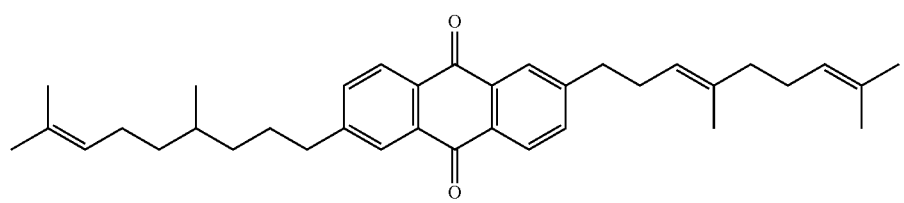

(Vb-22-viii)

Further, it is preferred that the process according to the present invention comprises crystallizing the compounds of formula (Va) and/or, preferably and, formula (Vb) from the mixture obtained in (v). Preferably, the crystallizing is carried out in an alcohol having from 1 to 12 carbon atoms.

Generally, the mixture obtained from (v), in particular the crystallized compounds of formula (Va) and/or, preferably and, formula (Vb), may be used as such for all suitable purposes, for example as mixture comprising one or more anthraquinone compounds for the preparation of hydrogen peroxide or as anthraquinone compounds for the preparation of hydrogen peroxide. Preferably, the mixture obtained from (v) is subjected to at least one further step, preferably including a treatment with a base.

Step (vi)

Preferably, the mixture obtained in (v) is subjected to a treating with an inorganic base according to (vi), wherein a mixture comprising the compounds of formula (Va) and/or, preferably and, formula (Vb). Preferred inorganic bases include, but are not restricted to, alkali metal bases and alkaline earth metal bases, preferably hydroxides, more preferably alkali metal bases, more preferably alkali metal hydroxides, more preferably potassium and/or sodium hydroxides. Thus, the treating in (vi) is preferably carried out in the presence of an inorganic base, preferably selected from the group consisting potassium hydroxide, sodium hydroxide, and a combination thereof. According to the present invention, it is particularly preferred that the inorganic base is potassium hydroxide.

Thus, it is particularly preferred that process according to the present invention further comprises vi) treating the mixture obtained in (v) with an inorganic base, preferably selected from the group consisting of potassium hydroxide, sodium hydroxide, and a combination thereof, wherein the inorganic base more preferably comprises, more preferably consists of, potassium hydroxide, obtaining a mixture comprising the compounds of formula (Va) and/or, preferably and, formula (Vb).

As far as the temperature at which the treating according to (vi) is carried out is concerned, no specific restrictions exist provided that the mixture obtained from (vi) comprises the compounds of formula (Va) and/or, preferably and, formula (Vb). Preferably, the treating according to (vi) is carried out at a temperature in the range of from 30 to 150° C., preferably from 40 to 100° C., more preferably from 45 to 90° C.

Further, it is preferred to crystallize the compounds of formula (Va) and/or, preferably and, formula (Vb) from the mixture obtained in (vi). Preferably, the crystallizing is carried out in an alcohol having from 1 to 12 carbon atoms.

Generally, the mixture obtained from (vi), in particular the crystallized compounds of formula (Va) and/or, preferably and, formula (Vb), may be used as such for all suitable purposes, for example as mixture comprising one or more anthraquinone compounds for the preparation of hydrogen peroxide or as anthraquinone compounds for the preparation of hydrogen peroxide.

Preferred Mixture

Further, the present invention relates to a mixture comprising the compounds of formula (Va)

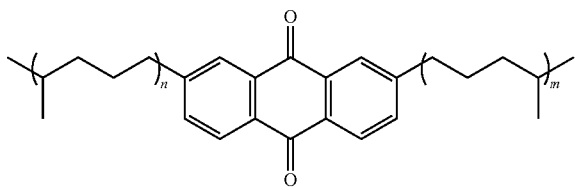

(Va)

and/or, preferably and, formula (Vb)

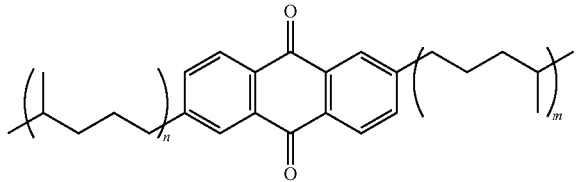

(Vb)

obtainable or obtained by a process according to the present invention, preferably by a process comprising (i) providing a mixture (A) comprising a compound of formula (I)

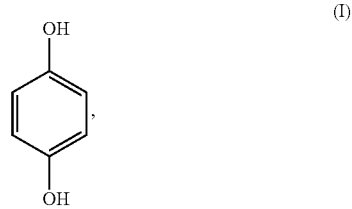

(I)

a compound of formula (II)

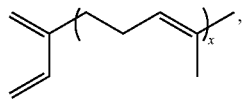

(II)

wherein x is 1, or a compound of formula (II) wherein x is 2, or a mixture of a compound of formula (II) wherein x is 1 and a compound of formula (II) wherein x is 2, a dehydrogenation catalyst, and a liquid solvent system;

(ii) treating the mixture (A) with an oxygen-containing gas obtaining a mixture (B) comprising a compound of formula (IIIa)

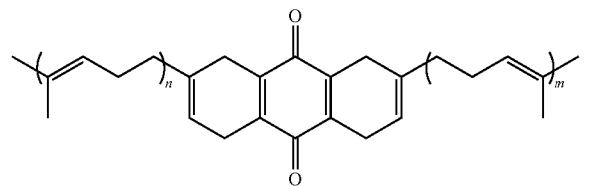

and/or, preferably and, a compound of formula (IIIb)

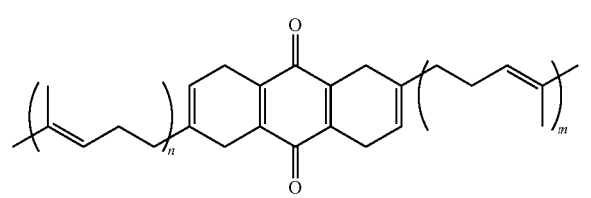

wherein n is 1 or 2 and wherein m is 1 or 2;

(iii) treating the mixture (B), optionally after work-up, with an oxygen-containing gas, obtaining a mixture (C) comprising a compound of formula (IVa)

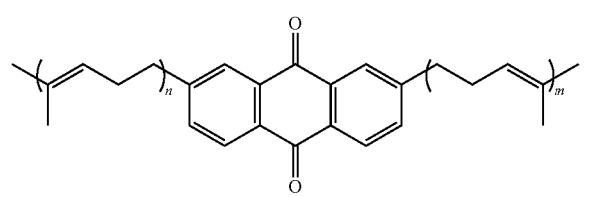

and/or, preferably and, a compound of formula (IVb)

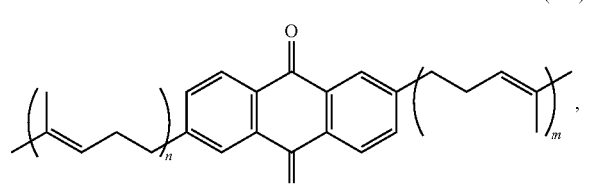

wherein n is 1 or 2 and wherein m is 1 or 2;

(iv) separating the compound of formula (IVa) and/or, preferably and, the compound of formula (IVb) from the mixture (C), obtaining a mixture of which at least 95 weight-%, preferably at least 97 weight-%, more preferably at least 99 weight-%, more preferably at least 99.9 weight-% consist of the compound of formula (IVa) and/or, preferably and, the compound of formula (IVb); wherein (iv) preferably comprises (iv.1) extracting the mixture (C), preferably with water;

(iv.2) optionally evaporating the organic solvent, preferably under reduced pressure after extracting the organic phase obtained from (iv.1), preferably with water obtaining a solid;

(iv.3) dissolving the solid obtained from (iv.2), preferably at a temperature in the range of from 50 to 250° C., more preferably from 60 to 200° C., wherein the organic solvent is preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof, more preferably selected from the group consisting of alcohols, having 1 to 12 carbon atoms;

(iv.4) cooling the solution obtained from (iv.3), preferably to temperature in the range of from −30 to +25° C., more preferably from −25 to +5° C., obtaining a suspension;

(iv.5) separating the solid from the suspension obtained from (iv.4);

(iv.6) preferably drying the solid obtained from (iv.5), preferably under vacuum;

(iv.7) optionally further purifying the solid obtained from (iv.5) or from (iv.6), preferably from (iv.6), preferably by chromatography;

(v) subjecting the mixture obtained in (iii), preferably the mixture obtained in (iv), more preferably the solid obtained in (iv), to a hydrogenation reaction, preferably in a solvent, in the presence of a hydrogenation catalyst, obtaining a mixture comprising a compound of formula (Va)

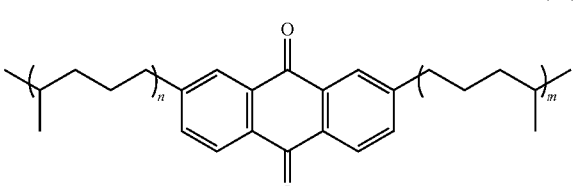

and/or, preferably and, a compound of formula (Vb)

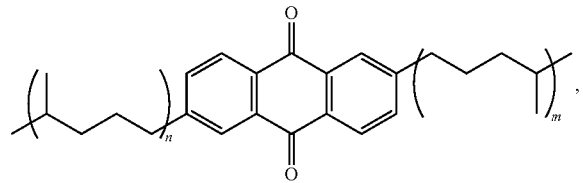
(Vb)

wherein n is 1 or 2 and wherein m is 1 or 2, with n and m preferably both being 1 or both being 2;

vi) preferably treating the mixture obtained in (v) with an inorganic base, preferably selected from the group consisting of potassium hydroxide, sodium hydroxide, and a combination thereof, wherein the inorganic base more preferably comprises, more preferably consists of, potassium hydroxide, obtaining a mixture comprising the compounds of formula (Va) and/or, preferably and, formula (Vb).

Preferred Compounds

Further, the present invention relates to a compound of formula (IVa)

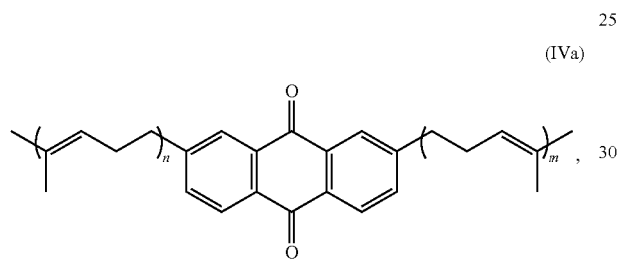
(IVa)

wherein n is 1 and m is 2.

Further, the present invention relates to a compound of formula (IVb)

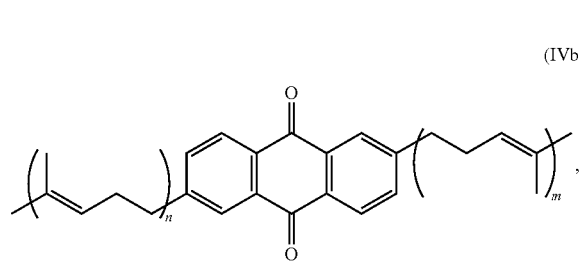
(IVb)

wherein n is 1 and m is 2.

Further, the present invention relates to a compound of formula (Va)

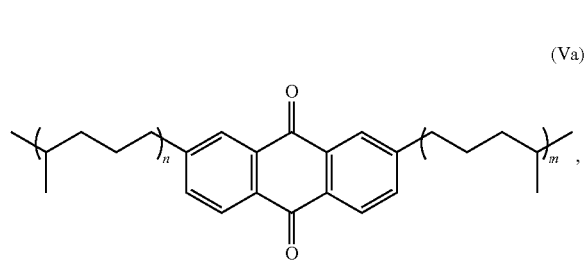
(Va)

wherein n is 1 and m is 2, or wherein n is 1 and m is 1, or wherein n is 2 and m is 2.

Further, the present invention relates to a compound of formula (Vb)

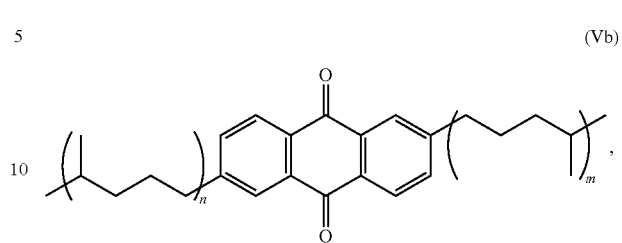
(Vb)

wherein n is 1 and m is 2, or wherein n is 1 and m is 1, or wherein n is 2 and m is 2.

Preferred Compositions

Further, the present invention relates to a composition comprising a compound of formula (IVa)

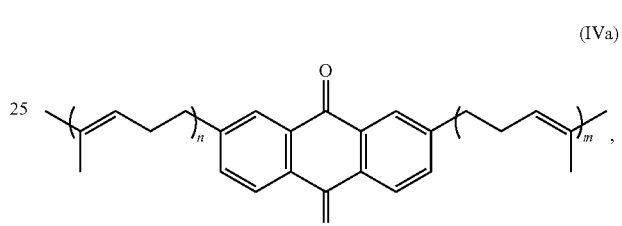
(IVa)

wherein n is 1 or 2 and wherein m is 1 or 2, with n and m preferably both being 1 or both being 2, more preferably both being 1, and/or, preferably and, a compound of formula (IVb)

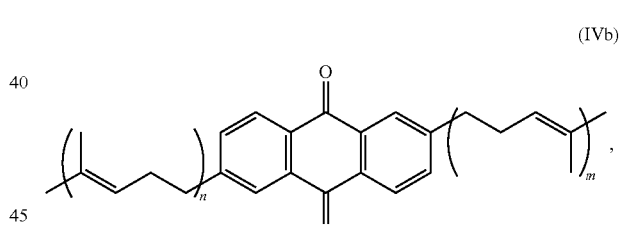
(IVb)

wherein n is 1 or 2 and wherein m is 1 or 2, with n and m preferably both being 1 or both being 2, more preferably both being 1, and wherein at least 95 weight-% of the mixture consist of compounds of formula (IVa) and formula (IVb).

Thus, the present invention relates to a composition comprising a compound of formula (IVa)

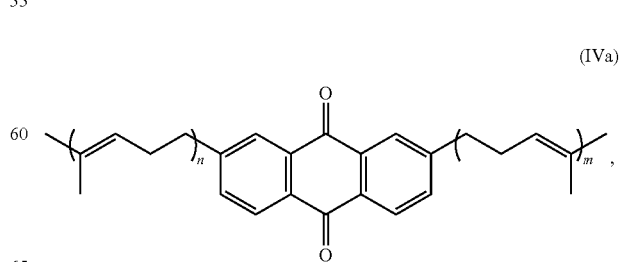
(IVa)

wherein n is 1 and m is 1, and/or, preferably and, a compound of formula (IVb)

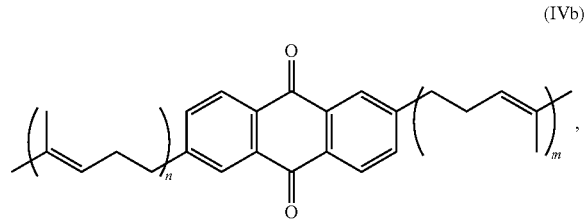
(IVb)

wherein n is 1 and m is 1, and wherein at least 95 weight-% of the mixture consist of compounds of formula (IVa) and formula (IVb).

Further, the present invention relates to a composition comprising a compound of formula (IVa)

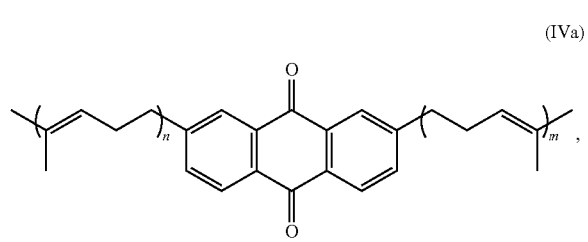
(IVa)

wherein n is 2 and m is 2,
and/or, preferably and, a compound of formula (IVb)

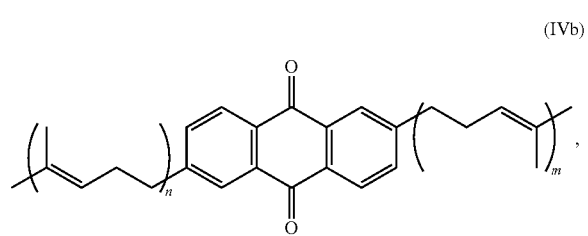
(IVb)

wherein n is 2 and m is 2, and wherein at least 95 weight-% of the mixture consist of compounds of formula (IVa) and formula (IVb).

Concerning the composition comprising the compounds of formula (IVa) wherein n is 2 and m is 2 and/or, preferably and formula (IVb) wherein n is 2 and m is 2, it is particularly preferred that at least 90 weight-%, preferably at least 92 weight-%, more preferably at least 94 weight-%, more preferably at least 96 weight-% such as at least 99 weight-% of the composition consist of the compounds of formula (IVa) and/or, preferably and formula (IVb).

Further, it is preferred that in the composition comprising the compounds of formula (IVa) wherein n is 2 and m is 2 and/or, preferably and formula (IVb) wherein n is 2 and m is 2, the molar ratio of the compound of formula (IVa) relative to the compound of formula (IVb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0:8:1 to 1.0:1 or from 0.9:1 to 1.1:1 or from 1.0:1 to 1.2:1.

Further, the present invention relates to a composition comprising a compound of formula (IVa)

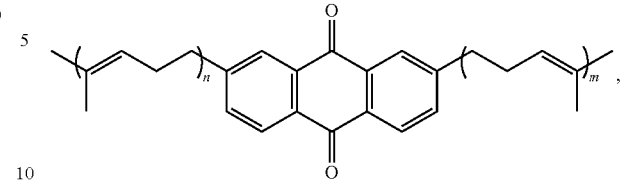
(IVa)

wherein n is 1 and m is 2,
and/or, preferably and, a compound of formula (IVb)

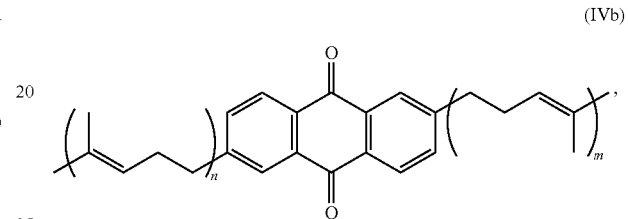
(IVb)

wherein n is 1 and m is 2, and wherein at least 95 weight-% of the mixture consist of compounds of formula (IVa) and formula (IVb).

Concerning the composition comprising the compounds of formula (IVa) wherein n is 1 and m is 2 and/or, preferably and formula (IVb) wherein n is 1 and m is 2, it is particularly preferred that at least 90 weight-%, preferably at least 92 weight-%, more preferably at least 4 weight-%, more preferably at least 96 weight-% such as at least 99 weight-% of the composition consist of the compounds of formula (IVa) and/or, preferably and formula (IVb).

Further, it is preferred that in the composition comprising the compounds of formula (IVa) wherein n is 1 and m is 2 and/or, preferably and formula (IVb) wherein n is 1 and m is 2, the molar ratio of the compound of formula (IVa) relative to the compound of formula (IVb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0.8:1 to 1.0:1 or from 0.9:1 to 1.1:1 or from 1.0:1 to 1.2:1.

Further, the present invention relates to a composition comprising a compound of formula (Va)

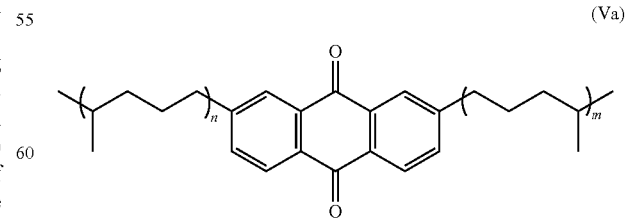
(Va)

wherein n is 1 or 2 and wherein m is 1 or 2, with n and m preferably both being 1 or both being 2, more preferably both being 1, and/or, preferably and, a compound of formula (Vb)

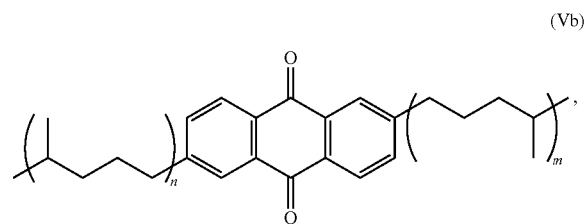

wherein n is 1 or 2 and wherein m is 1 or 2, with n and m preferably both being 1 or both being 2, more preferably both being 1, and wherein at least 95 weight-% of the composition consist of compounds of formula (Va) and formula (Vb).

Thus, the present invention relates to a composition comprising a compound of formula (Va)

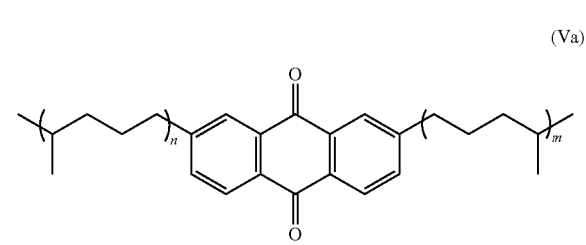

wherein n is 1 and m is 1,
and/or, preferably and, a compound of formula (Vb)

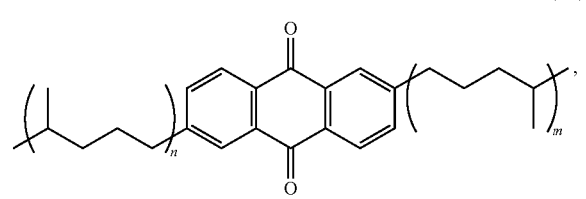

wherein n is 1 and m is 1, and wherein at least 95 weight-% of the mixture consist of compounds of formula (Va) and formula (Vb).

Concerning the composition comprising the compounds of formula (Va) wherein n is 1 and m is 1 and/or, preferably and formula (Vb) wherein n is 1 and m is 1, it is particularly preferred that at least 90 weight-%, preferably at least 92 weight-%, more preferably at least 94 weight-%, more preferably at least 96 weight-% such as at least 99 weight-% of the composition consist of the compounds of formula (Va) and/or, preferably and formula (Vb).

Further, it is preferred that in the composition comprising the compounds of formula (Va) wherein n is 1 and m is 1 and/or, preferably and formula (Vb) wherein n is 1 and m is 1, the molar ratio of the compound of formula (Va) relative to the compound of formula (Vb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0:8:1 to 1.0:1 or from 0.9:1 to 1.1:1 or from 1.0:1 to 1.2:1.

Further, the present invention relates to a composition comprising a compound of formula (Va)

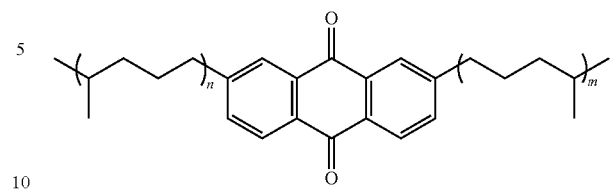

wherein n is 2 and m is 2,
and/or, preferably and, a compound of formula (Vb)

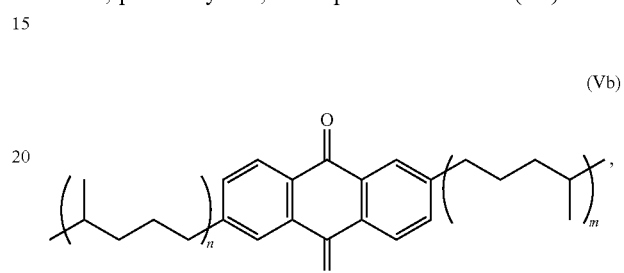

wherein n is 2 and m is 2, and wherein at least 95 weight-% of the mixture consist of compounds of formula (Va) and formula (Vb).

Concerning the composition comprising the compounds of formula (Va) wherein n is 2 and m is 2 and/or, preferably and formula (Vb) wherein n is 2 and m is 2, it is particularly preferred that at least 90 weight-%, preferably at least 92 weight-%, more preferably at least 94 weight-%, more preferably at least 96 weight-% such as at least 99 weight-% of the composition consist of the compounds of formula (Va) and/or, preferably and formula (Vb).

Further, it is preferred that in the composition comprising the compounds of formula (Va) wherein n is 2 and m is 2 and/or, preferably and formula (Vb) wherein n is 2 and m is 2, the molar ratio of the compound of formula (Va) relative to the compound of formula (Vb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0:8:1 to 1.0:1 or from 0.9:1 to 1.1:1 or from 1.0:1 to 1.2:1.

Further, the present invention relates to a composition comprising a compound of formula (Va)

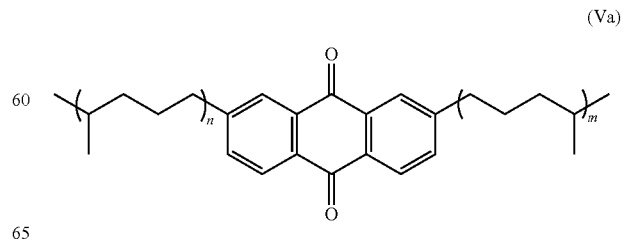

wherein n is 1 and m is 2, and/or, preferably and, a compound of formula (Vb)

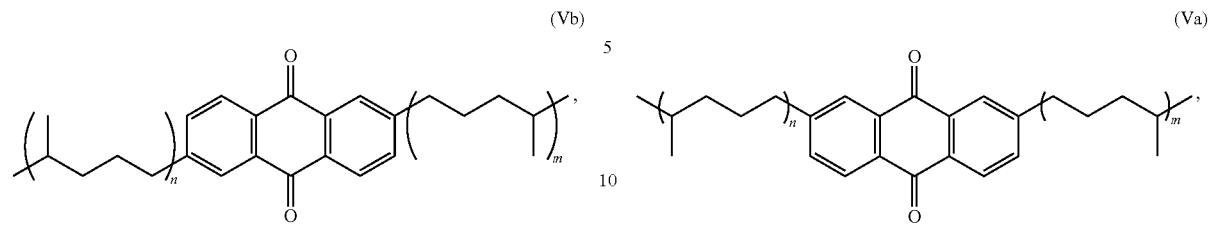
(Vb)

wherein n is 1 and m is 2, and wherein at least 95 weight-% of the composition consist of compounds of formula (Va) and formula (Vb).

Concerning the composition comprising the compounds of formula (Va) wherein n is 1 and m is 2 and/or, preferably and formula (Vb) wherein n is 1 and m is 2, it is particularly preferred that at least 90 weight-%, preferably at least 92 weight-%, more preferably at least 94 weight-%, more preferably at least 96 weight-% such as at least 99 weight-% of the composition consist of the compounds of formula (Va) and/or, preferably and formula (Vb).

Further, it is preferred that in the composition comprising the compounds of formula (Va) wherein n is 1 and m is 2 and/or, preferably and formula (Vb) wherein n is 1 and m is 2, the molar ratio of the compound of formula (Va) relative to the compound of formula (Vb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0:8:1 to 1.0:1 or from 0.9:1 to 1.1:1 or from 1.0:1 to 1.2:1.

Preferred Uses

The compounds of the present invention, preferably the compound of formula (IVa)

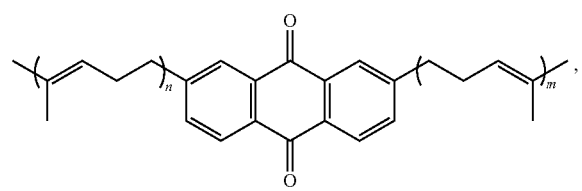
(IVa)

and/or the compound of formula (IVb)

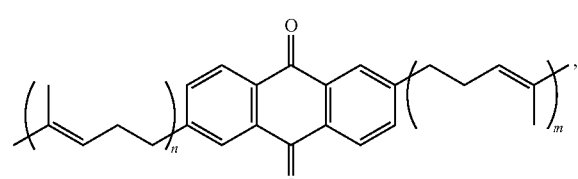
(IVb)

and/or the compound of formula (Va)

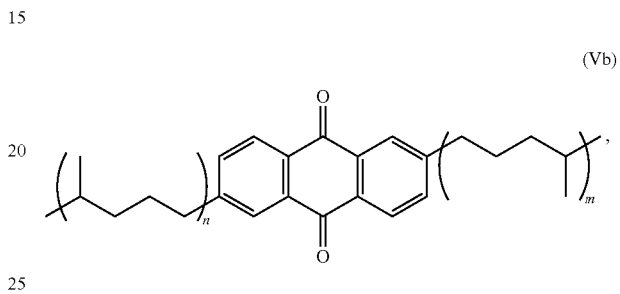
(Va)

and/or the compound of formula (Vb)

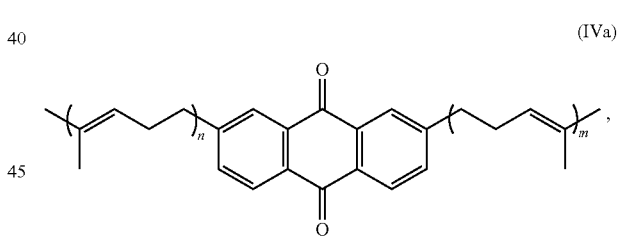
(Vb)

wherein n is 1 and m is 2, or wherein n is 1 and m is 1, or wherein n is 2 and m is 2, or a composition comprising a compound of formula (IVa) and/or, preferably and, a compound of formula (IVb) wherein n is 1 and m is 2, or wherein n is 1 and m is 1, or wherein n is 2 and m is 2, or a composition comprising a compound of formula (Va) and/or, preferably and, a compound of formula (Vb) wherein n is 1 and m is 2, or wherein n is 1 and m is 1, or wherein n is 2 and m is 2 as described above, can be used for every conceivable purpose.

Preferably, the present invention relates to the use of a compound of formula (IVa)

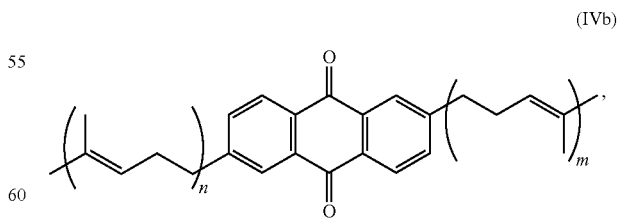
(IVa)

wherein n is 1 and m is 2, or wherein n is 1 and m is 1, or wherein n is 2 and m is 2, or of a compound of formula (IVb)

(IVb)

wherein n is 1 and m is 2, or wherein n is 1 and m is 1, or wherein n is 2 and m is 2, or of a composition comprising a compound of formula (IVa) and a compound of formula (IVb), preferably a composition comprising a compound of formula (IVa) and a compound of formula (IVb) as described above, for the preparation of hydrogen peroxide, preferably as anthraquinone compound in an anthraquinone process for the preparation of hydrogen peroxide.

Further, the present invention relates to the use of a compound of formula (Va)

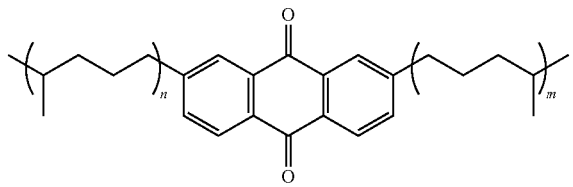

(Va)

wherein n is 1 and m is 2, or wherein n is 1 and m is 1, or wherein n is 2 and m is 2, or of a compound of formula (Vb)

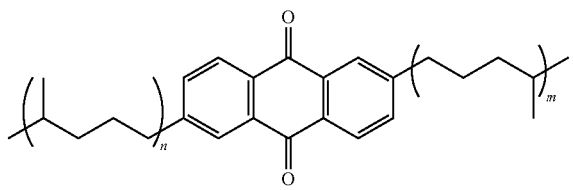

(Vb)

wherein n is 1 and m is 2, or wherein n is 1 and m is 1, or wherein n is 2 and m is 2, or of a composition comprising a compound of formula (Va) and a compound of formula (Vb), preferably a composition comprising a compound of formula (Va) and a compound of formula (Vb) as described above, for the preparation of hydrogen peroxide, preferably as anthraquinone compound in an anthraquinone process for the preparation of hydrogen peroxide.

Process for the Preparation of Hydrogen Peroxide

Without wanting to be bound by any theory, it is believed that the compounds according to the present invention, in particular the compounds of formula (IVa), formula (IVb), formula (Va) and formula (Vb), wherein n is 1 and m is 2, or wherein n is 1 and m is 1, or wherein n is 2 or m is 2, are especially stable against ring-hydrogenation if used as anthraquinone starting materials in processes for the preparation of hydrogen peroxide.

Thererfore, the present invention also relates to a process for the preparation of hydrogen peroxide, comprising (I) providing a compound of formula (IVa)

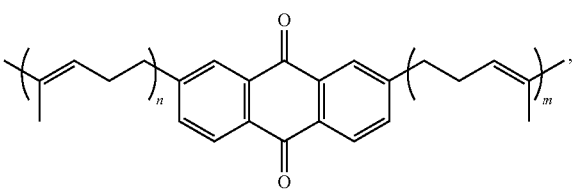

(IVa)

wherein n is 1 and m is 2, or wherein n is 1 and m is 1, or wherein n is 2 and m is 2, or a compound of formula (IVb)

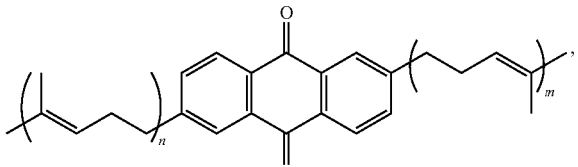

(IVb)

wherein n is 1 and m is 2, or wherein n is 1 and m is 1, or wherein n is 2 and m is 2, or a compound of formula (Va)

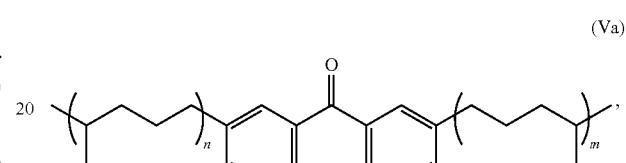

(Va)

wherein n is 1 and m is 2, or wherein n is 1 and m is 1, or wherein n is 2 and m is 2, or a compound of formula (Vb)

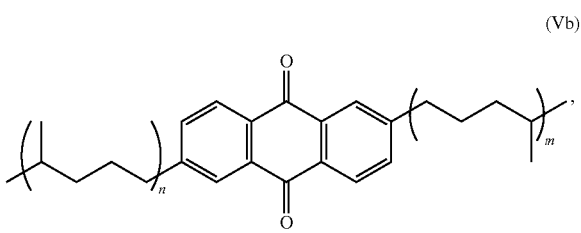

(Vb)

wherein n is 1 and m is 2, or wherein n is 1 and m is 1, or wherein n is 2 and m is 2, or a composition comprising at least one of the compounds of formula (IVa) and (Va) and at least one of the compounds of formula (IVb) and (Vb), preferably a composition comprising a compound of formula (IVa) and a compound of formula (IVb) or a composition comprising a compound of formula (Va) and a compound of formula (Vb), more preferably a composition as described above;

(II) preparing a mixture comprising the compound or the composition, preferably the composition, provided in (I) dissolved in an organic solvent, wherein the solvent is preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N- dialkyl carbamates, N-alkyl carbonamides, tetraalkyl ureas, cycloalkyl ureas, and a mixture of two or more thereof, and further comprising a hydrogenation catalyst;

(III) subjecting the mixture prepared in (II) to a hydrogenation reaction, obtaining a mixture comprising a compound of formula (VIa)

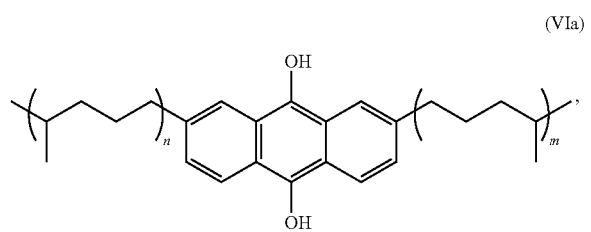

(VIa)

or comprising a compound of formula (VIb)

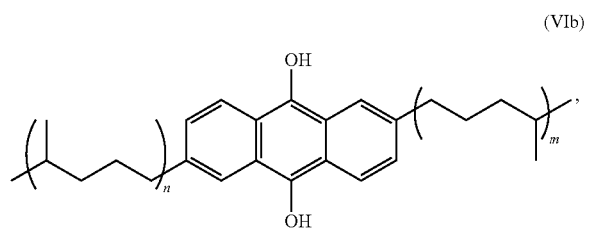

(VIb)

or comprising a compound of formula (VIa) and a compound formula (VIb), preferably comprising a compound of formula (VIa) and a compound of formula (VIb);

(IV) subjecting the mixture obtained in (III) to an oxidation reaction in the presence of an oxygen containing gas, obtaining a mixture comprising the compound of formula (Va), or the compound of formula (Vb), or the compound of formula (Va) and the compound of formula (Vb), preferably comprising the compound of formula (Va) and the compound of formula (Vb), and further comprising hydrogen peroxide;

(V) separating the hydrogen peroxide from the mixture obtained in (IV), obtaining a mixture comprising hydrogen peroxide and a mixture comprising the compound of formula (Va), or the compound of formula (Vb), or the compound of formula (Va) and the compound of formula (Vb), preferably comprising the compound of formula (Va) and the compound of formula (Vb);

(VI) preferably subjecting the mixture obtained in (V), comprising the compound of formula (Va), or the compound of formula (Vb), or the compound of formula (Va) and the compound of formula (Vb), preferably comprising the compound of formula (Va) and the compound of formula (Vb), to at least one repetition of the sequence of steps (III) to (V).

In particular in case the process for the preparation of hydrogen peroxide is carried out by use of a compound of formula (IVa) or a compound of formula (IVb) or a mixture comprising a compound of formula (IVa) or a compound of formula (IVb), preferably a composition comprising a compound of formula (IVa) or a compound of formula (IVb), intermediate compounds of the following formulas can be obtained, depending on the specific values of the indices n and m of the compound or compounds of formula (IIIa) and/or (IIIb) and, therefore, the value of the index x of the compound or the compounds of formula (II):

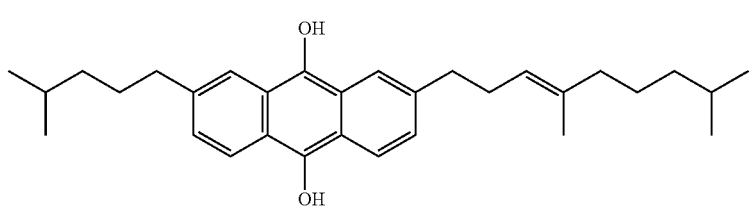

(VIa-12-i)

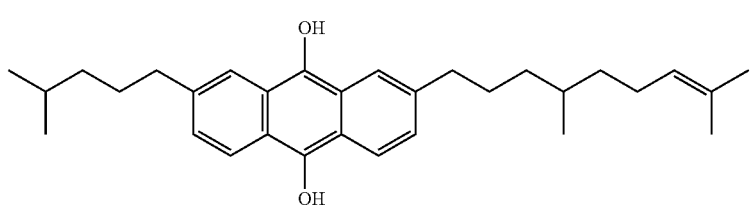

(VIa-12-ii)

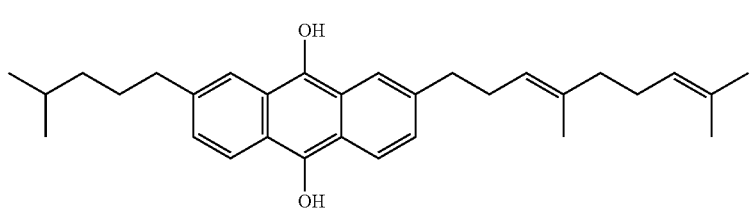

(VIa-12-iii)

-continued
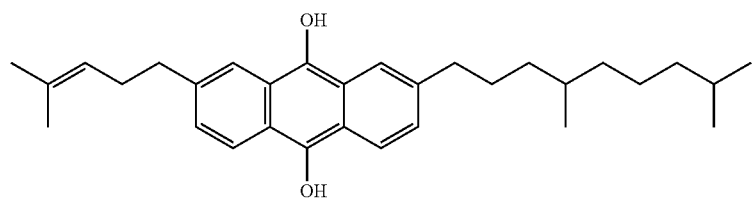
(VIa-12-iv)
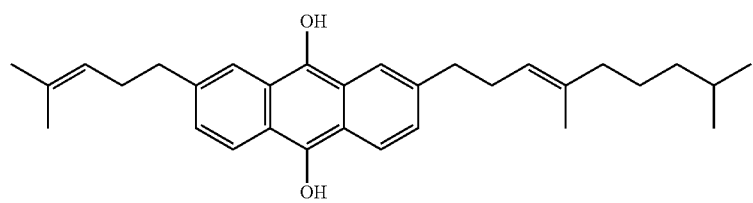
(VIa-12-v)
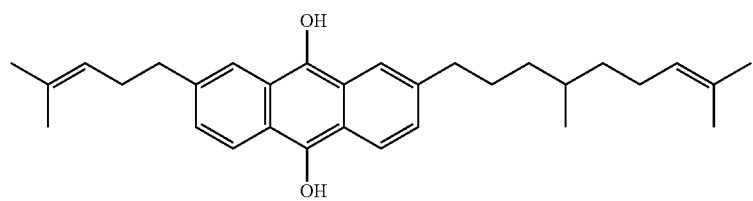
(VIa-12-vi)
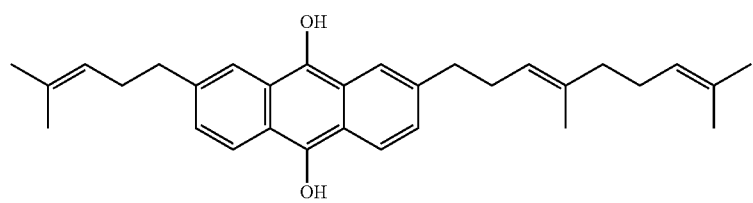
(VIa-12-vii)
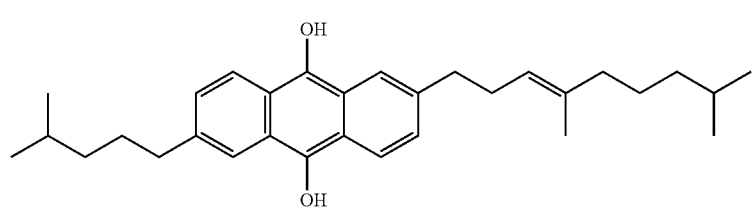
(VIb-12-i)
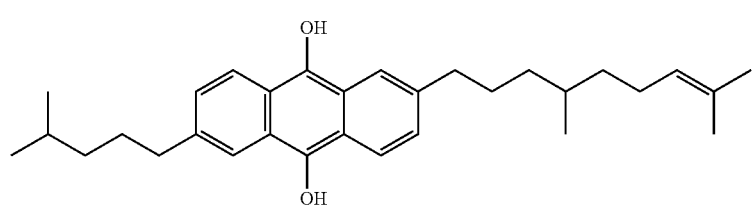
(VIb-12-ii)
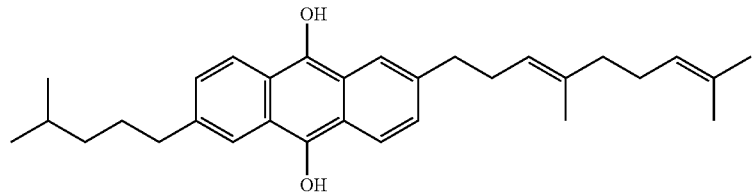
(VIb-12-iii)

-continued
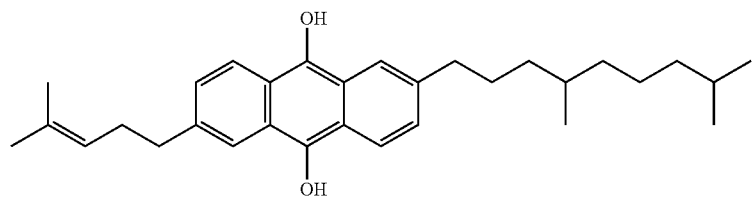
(VIb-12-iv)
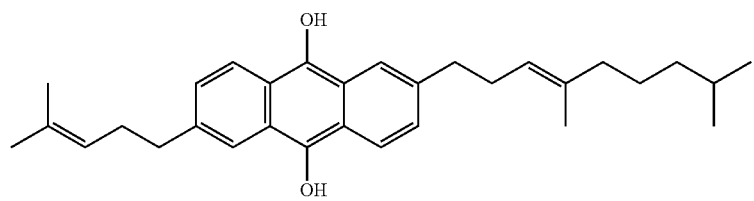
(VIb-12-v)
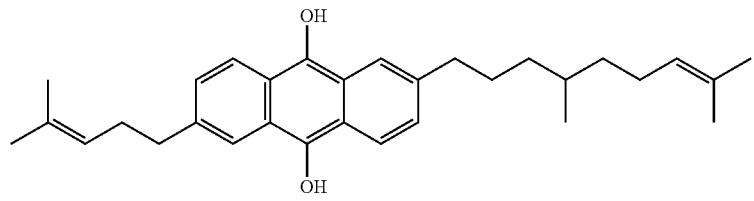
(VIb-12-vi)
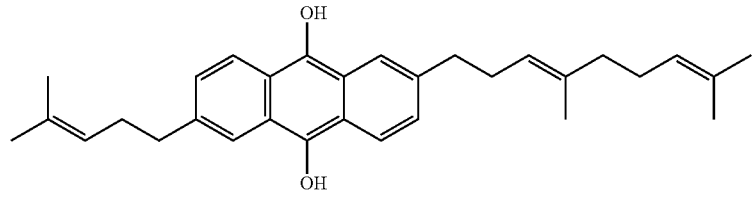
(VIb-12-vii)
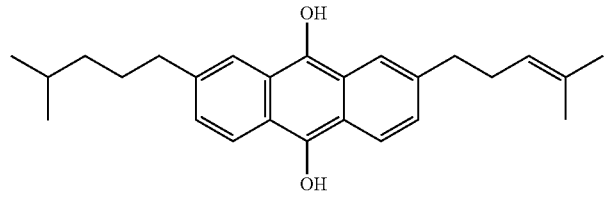
(VIa-11-i)
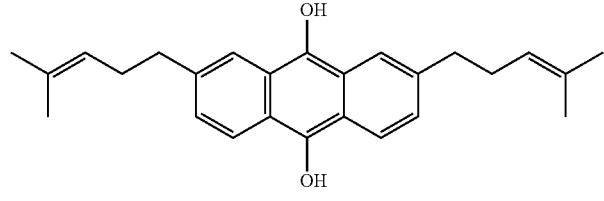
(VIa-11-ii)
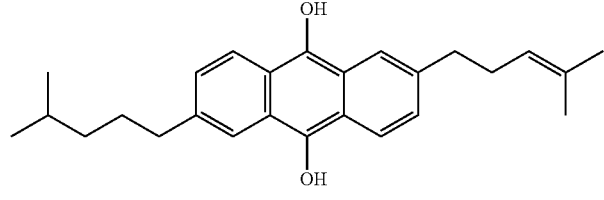
(VIb-11-i)
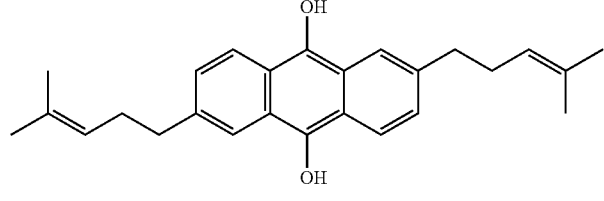
(VIb-11-ii)

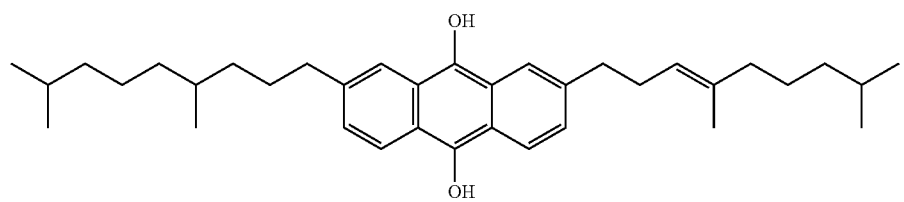
(VIa-22-i)
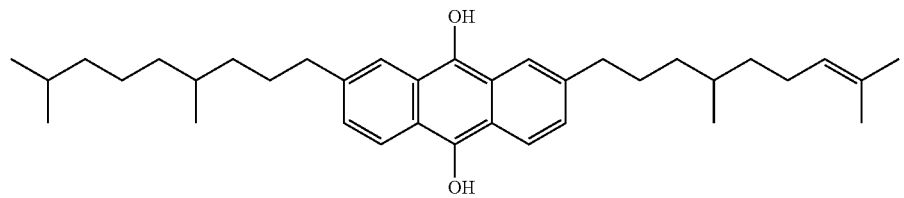
(VIa-22-ii)
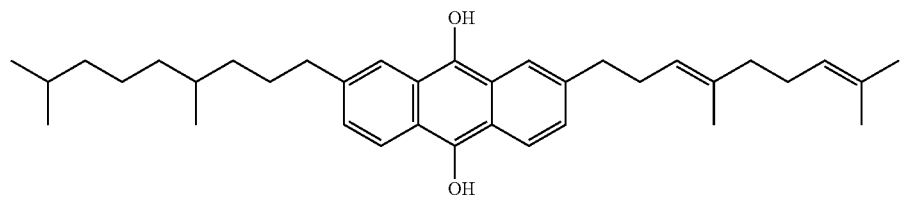
(VIa-22-iii)
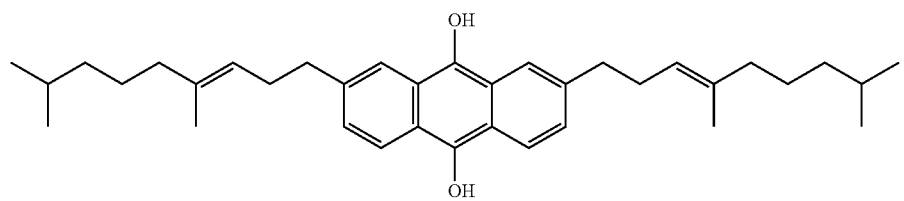
(VIa-22-iv)
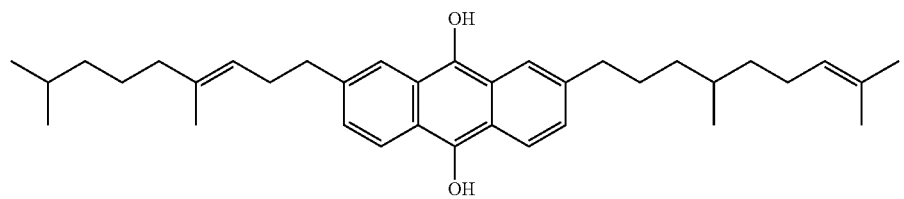
(VIa-22-v)
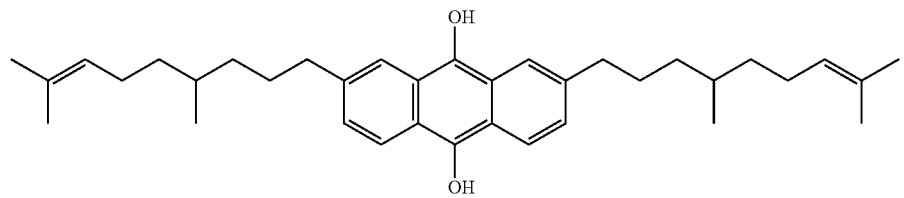
(VIa-22-vi)
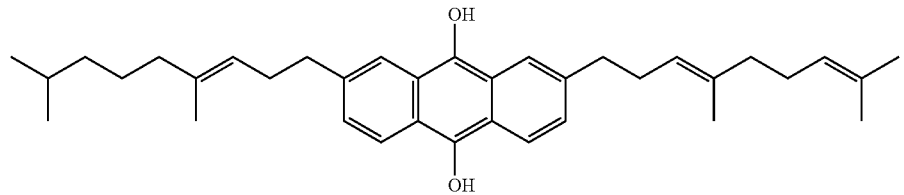
(VIa-22-vii)
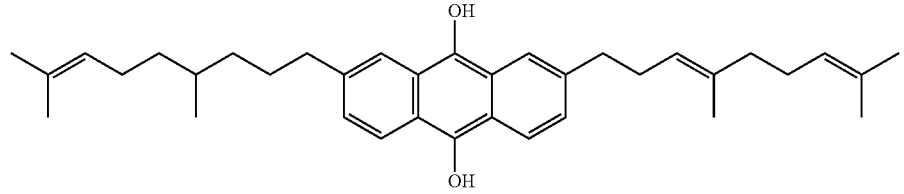
(VIa-22-viii)

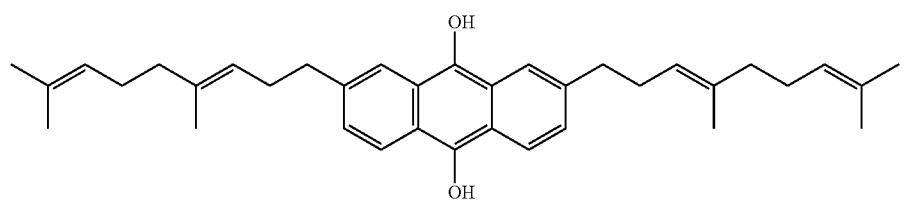
(VIa-22-ix)
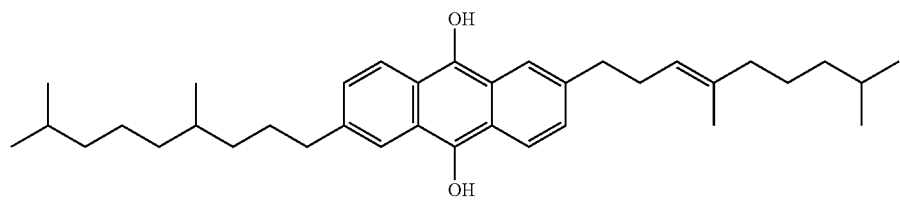
(VIb-22-i)
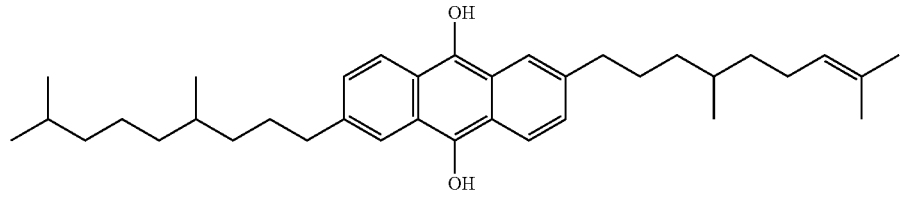
(VIb-22-ii)
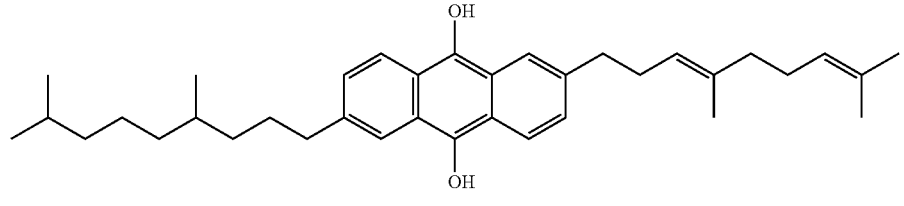
(VIb-22-iii)
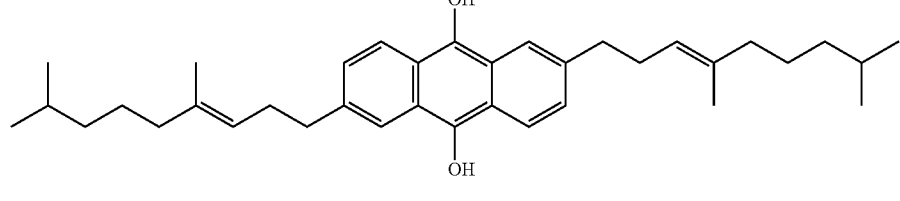
(VIb-22-iv)
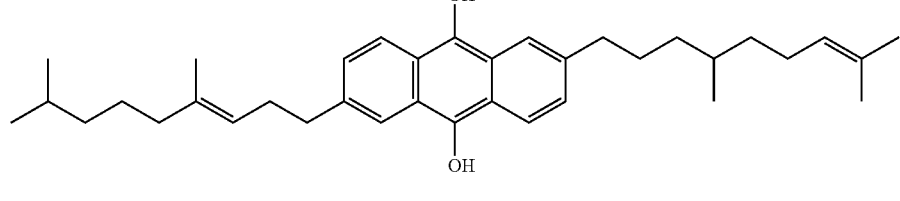
(VIb-22-v)
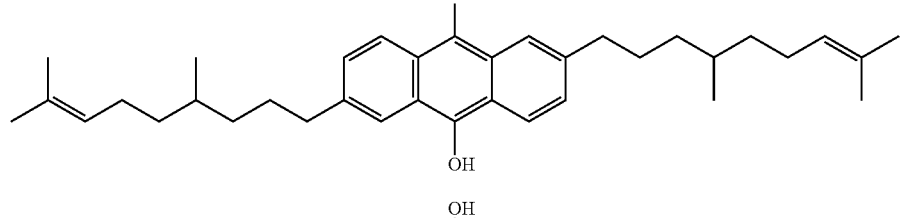
(VIb-22-vi)
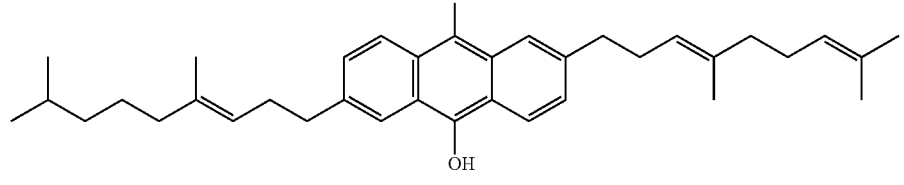
(VIb-22-vii)

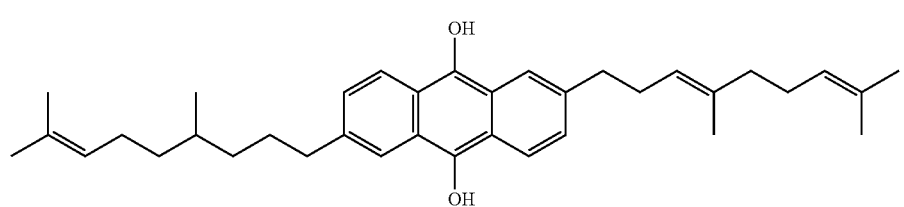
(VIb-22-viii)

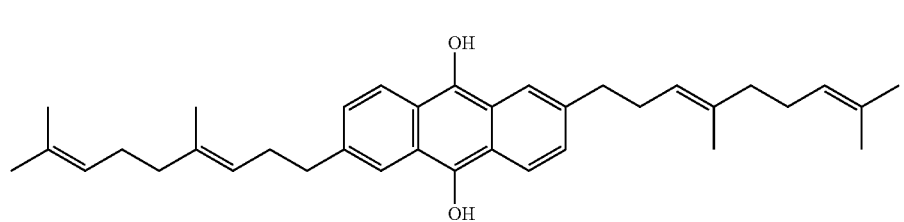
(VIb-22-ix)

Generally, there are no specific restrictions how the compound of formula (IVa), or the compound of formula (IVb), or the compound of formula (Va), or the compound of formula (Vb), or a composition comprising at least one of the compounds of formula (IVa) and (Va) and at least one of the compounds of formula (IVb) and (Vb), preferably a composition comprising a compound of formula (IVa) and a compound of formula (IVb) or a composition comprising a compound of formula (Va) and a compound of formula (Vb), more preferably a composition as described above, is provided in (I). For example, any conceivable process for synthesizing such a compound can be employed for providing the compound of formula (IVa), or the compound of formula (IVb), or the compound of formula (Va), or the compound of formula (Vb) or the composition comprising such compounds.

Preferably, according to (I), the composition comprising a compound of formula (IVa) and a compound of formula (IVb) is provided by a process comprising the steps (i), (ii) and (iii) according to the present invention.

Further, it is preferred that according to (I), the composition comprising a compound of formula (Va) and a compound of formula (Vb) is provided by a process comprising the steps (i), (ii), (iii), (iv), (v) and (vi).

According to the present invention, in (I), it is preferred to provide a composition comprising a compound of formula (IVa)

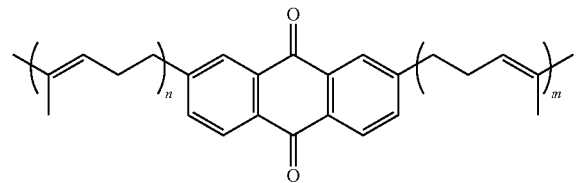
(IVa)

wherein n is 1 and m is 1, or wherein n is 2 and m is 2, and a compound of formula (IVb)

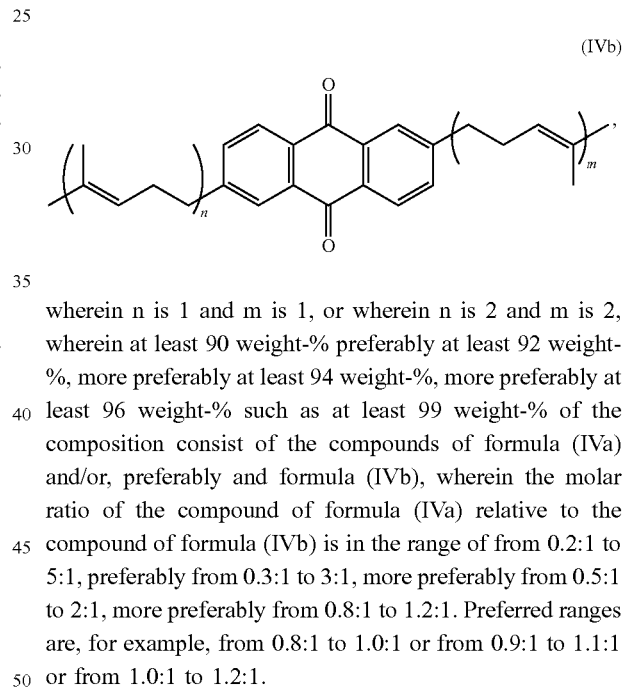

wherein n is 1 and m is 1, or wherein n is 2 and m is 2, wherein at least 90 weight-% preferably at least 92 weight-%, more preferably at least 94 weight-%, more preferably at least 96 weight-% such as at least 99 weight-% of the composition consist of the compounds of formula (IVa) and/or, preferably and formula (IVb), wherein the molar ratio of the compound of formula (IVa) relative to the compound of formula (IVb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0.8:1 to 1.0:1 or from 0.9:1 to 1.1:1 or from 1.0:1 to 1.2:1.

According to the present invention, in (I), it is particularly preferred to provide a composition comprising a compound of formula (Va)

(Va)

wherein n is 1 and m is 1, or wherein n is 2 and m is 2, and a compound of formula (Vb)

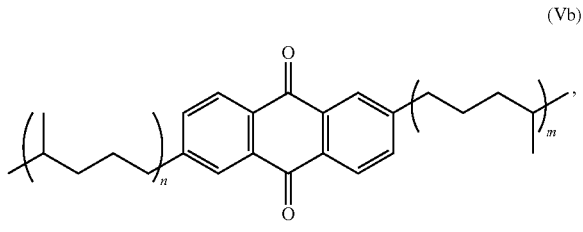

(Vb)

wherein n is 1 and m is 1, or wherein n is 2 and m is 2, wherein at least 90 weight-% preferably at least 92 weight-%, more preferably at least 94 weight-%, more preferably at least 96 weight-% such as at least 96 weight-% of the composition consist of the compounds of formula (IVa) and/or, preferably and formula (IVb), wherein the molar ratio of the compound of formula (IVa) relative to the compound of formula (IVb) is in the range of from 0.2:1 to 5:1, preferably from 0.3:1 to 3:1, more preferably from 0.5:1 to 2:1, more preferably from 0.8:1 to 1.2:1. Preferred ranges are, for example, from 0.8:1 to 1.0:1 or from 0.9:1 to 1.1:1 or from 1.0:1 to 1.2:1.

Thereafter, according to (II), a mixture is preferably prepared comprising the compound or the composition, preferably the composition, provided in (I) dissolved in an organic solvent, wherein the mixture further comprises a hydrogenation catalyst.

In general, there are no specific restrictions concerning the nature of the hydrogenation catalyst provided the catalyst is able to catalyze the hydrogenation reaction according to (ii). Preferably, the hydrogenation catalyst comprises one or more metals active in hydrogenation, wherein more preferably, the one or more metals are selected from the group consisting of at least on element selected from the group of transition metals and a combination of two or more thereof, wherein the hydrogenation catalyst more preferably comprises Pd, Rh, Ru, Ni, Re, Os, Ir, Pt, Au, Ag, and a combination of two or more thereof, more preferably Pd, Rh, Ru, Ni, and a combination of two or more thereof, wherein more preferably, the one or more metals comprise Pd, even more preferably consists of Pd.

Further, it is preferred that one or more metals comprised in the hydrogenation catalyst according to (II) is supported on a support. As regards this support, no specific restrictions exist concerning the nature of the support provided that the hydrogenation catalyst is able to catalyze the hydrogenation reaction according to (III). Preferably, the support comprises at least on element selected from the group consisting of aluminum, barium, calcium, cerium, zirconium, titanium and silicon. More preferably the support comprises at least one compound selected from the group consisting of aluminum oxide, barium sulfate, calcium carbonate, cerium (IV) oxide, silicon oxide and zirconium(IV) oxide.

Thus, it is particularly preferred that the hydrogenation catalyst according to (II) comprises palladium preferably supported on a support preferably comprising at least on element selected from the group consisting of aluminum, barium, calcium, cerium, zirconium, titanium and silicon, more preferably comprising at least one compound selected from the group consisting of aluminum oxide, barium sulfate, calcium carbonate, cerium(IV) oxide, silicon oxide and zirconium(IV) oxide.

Optionally, (III) further comprises separating the hydrogenation catalyst from the mixture comprising a compound of formula (VIa)

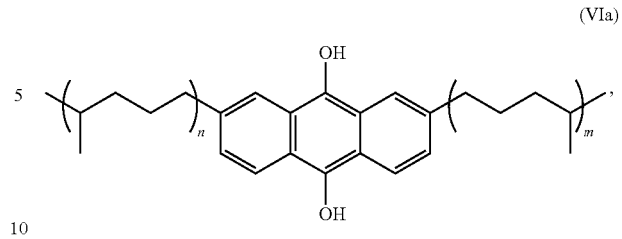

(VIa)

or comprising a compound of formula (VIb)

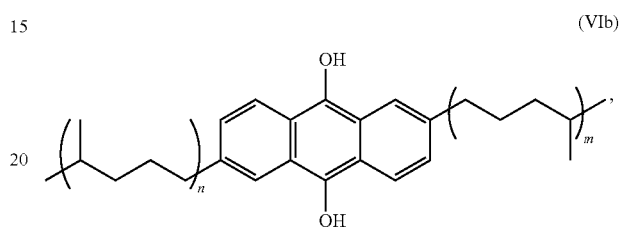

(VIb)

or comprising a compound of formula (VIa) and a compound formula (VIb), preferably comprising a compound of formula (VIa) and a compound of formula (VIb).

The mixture obtained in (III), preferably after separating the hydrogenation catalyst, is subjected an oxidation reaction according to (IV). It is particularly preferred that the mixture comprises a compound of formula (VIa)

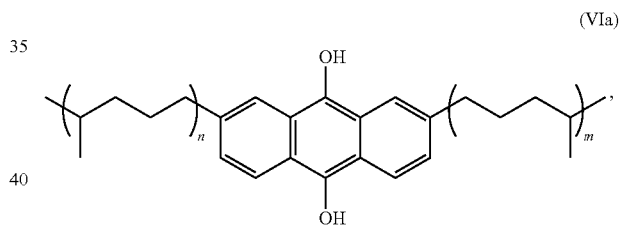

(VIa)

or comprises a compound of formula (VIb)

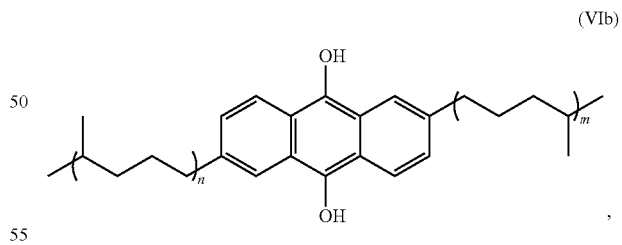

(VIb)

or comprises a compound of formula (VIa) and a compound formula (VIb), preferably comprises a compound of formula (VIa) and a compound of formula (VIb), wherein the molar ratio of the compound of formula (VIa) relative to the compound of formula (VIb) is in the range of from 0.2:1 to 5:1, preferably from 0.3:1 to 3:1, more preferably from 0.5:1 to 2:1, more preferably from 0.8:1 to 1.2:1, is subjected to an oxidation reaction according to (IV), wherein a mixture comprising the compound of formula (Va), or the compound of formula (Vb), or the compound of formula (Va) and the compound of formula (Vb), preferably comprising the compound of formula (Va) and the compound of formula (Vb), wherein the molar ratio of the compound of formula (Va) relative to the compound of formula (Vb) is in the range of from 0.2:1 to 5:1, preferably from 0.3:1 to 3:1, more preferably from 0.5:1 to 2:1, more preferably from 0.8:1 to 1.2:1, is obtained, and wherein the mixture further comprises hydrogen peroxide. Preferred ranges are, for example, from 0.8:1 to 1.0:1 or from 0.9:1 to 1.1:1 or from 1.0:1 to 1.2:1.

As regards the separation according to (V), all methods of separating the hydrogen peroxide from the mixture obtained in (V) are conceivable. Preferably, the hydrogen peroxide is separated from the mixture obtained in (IV) by extraction, more preferably by extraction with an aqueous solution, more preferably by extraction with water, wherein a mixture comprising hydrogen peroxide obtained is obtained.

Preferably, at least 1 weight-%, more preferably at least 5 weight-%, more preferably at least 10 weight-%, more preferably at least 20 weight-%, more preferably at least 30 weight-% of the mixture comprising hydrogen peroxide obtained according to (V) consist of hydrogen peroxide.

After the separation according to (V), the mixture obtained in (V) comprising the compound of formula (Va), or the compound of formula (Vb), or the compound of formula (Va) and the compound of formula (Vb), preferably comprising the compound of formula (Va) and the compound of formula (Vb), is subjected to at least one repetition of the sequence of steps (III) to (V), wherein prior subjecting the mixture obtained in (V) to a hydrogenation reaction according to (III), a hydrogenation catalyst is added to the mixture obtained in (V).

The present invention also relates to a mixture comprising hydrogen peroxide, obtainable or obtained by a process for the preparation of hydrogen peroxide as described above, preferably obtainable or obtained in step (V) of a process for the preparation of hydrogen peroxide as described above.

The mixture comprising hydrogen peroxide according to the present invention can be used for every conceivable purpose. Preferably, the mixture comprising hydrogen peroxide according to the present invention is used for the preparation of propylene oxide, a propylene glycol, a polyol and/or a polyurethane. Thus, the present invention relates to the use of a mixture comprising hydrogen peroxide as described above for the preparation of propylene oxide, a propylene glycol, a polyol and/or a polyurethane.

The present invention is further illustrated by the following list of embodiments, including all combinations of embodiments as indicated by the respective dependencies and references.

1. A process for the preparation of an anthraquinone derivative comprising
   (i) providing a mixture (A) comprising a compound of formula (I)

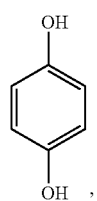

(I)

a compound of formula (II)

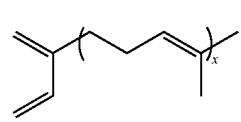

(II)

wherein x is 1, or a compound of formula (II) wherein x is 2, or a mixture of a compound of formula (II) wherein x is 1 and a compound of formula (II) wherein x is 2, a dehydrogenation catalyst, and a liquid solvent system;

(ii) treating the mixture (A) with an oxygen-containing gas obtaining a mixture (B) comprising a compound of formula (IIIa)

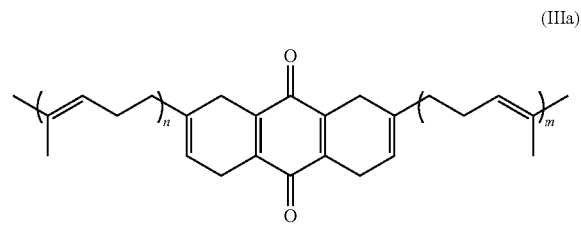

(IIIa)

and/or, preferably and, a compound of formula (IIIb)

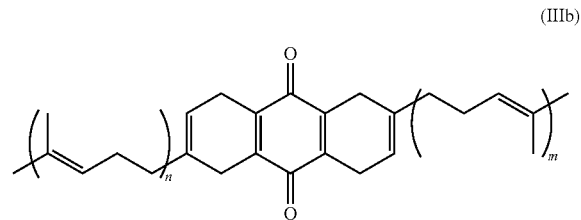

(IIIb)

wherein n is 1 or 2 and wherein m is 1 or 2;

(iii) treating the mixture (B), optionally after work-up, with an oxygen-containing gas, obtaining a mixture (C) comprising a compound of formula (IVa)

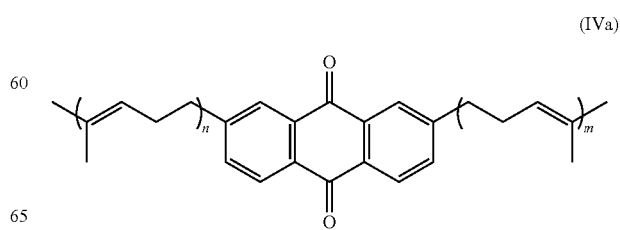

(IVa)

and/or, preferably and, a compound of formula (IVb)

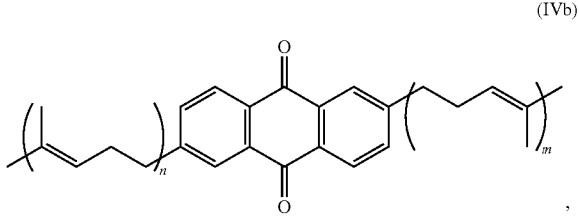

(IVb)

wherein n is 1 or 2 and wherein m is 1 or 2.
2. The process of embodiment 1, wherein the mixture (A) provided in (i) comprises a compound of formula (II) wherein x is 1 and the mixture (B) obtained in (ii) comprises a compound of formula (IIIa) and a compound of formula (IIIb) wherein n is 1 and m is 1, and the mixture (C) obtained in (iii) comprises a compound of formula (IVa) and a compound of formula (IVb) wherein n is 1 and m is 1.
3. The process of embodiment 1, wherein the mixture (A) provided in (i) comprises a compound of formula (II) wherein x is 2 and the mixture (B) obtained in (ii) comprises a compound of formula (IIIa) and a compound of formula (IIIb) wherein n is 2 and m is 2, and the mixture (C) obtained in (iii) comprises a compound of formula (IVa) and a compound of formula (IVb) wherein n is 2 and m is 2.
4. The process of any of embodiments 1 to 3, wherein the sequence of steps (i) to (iii) is carried out as a one-pot process.
5. The process of any of embodiments 1 to 4, wherein the dehydrogenation catalyst according to (i) comprises at least on element selected from the group of transition metals and a combination of two or more thereof, wherein the dehydrogenation catalyst more preferably comprises comprises copper and at least one additional element selected from the group consisting of lithium, zinc, zirconium, aluminum, and a combination of two or more thereof, wherein the dehydrogenation catalyst preferably comprises a combination of copper, and lithium or a combination of copper, zinc, zirconium and aluminum.
6. The process of any of embodiments 1 to 5, wherein providing the mixture (A) according to (i) comprises admixing the compound of formula (I) with the compound of formula (II) at a molar ratio of the compound of formula (I) relative to the compound of formula (II) in the range of from 0.1:1 to 1:1, preferably from 0.2:1 to 1:1, more preferably from 0.3:1 to 1:1.
7. The process of any of embodiments 1 to 6, wherein the liquid solvent system according to (i) comprises an organic solvent, preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof,
8. The process of embodiment 7, wherein the liquid solvent system according to (i) further comprises water.
9. The process of embodiment 8, wherein in the liquid solvent system, the molar ratio of organic solvent relative to water is in the range of from 100:1 to 0.01:1, preferably from 50:1 to 0.02:1, more preferably from 30:1 to 0.03:1.
10. The process of any of embodiments 1 to 9, wherein prior to (ii), the mixture (A) is heated to a temperature in the range of from 30 to 150° C., preferably from 40 to 100° C., more preferably from 45 to 90° C.
11. The process of any of embodiments 1 to 9, wherein the providing according to (i) comprises
(i.1) preparing a mixture (A.1) comprising at least a portion of the dehydrogenation catalyst and at least a portion of the liquid solvent system;
(i.2) adding at least a portion of the compound of formula (I) and at least a portion of the compound of formula (II) to the mixture prepared in (i.1).
12. The process of embodiment 11, wherein prior to (i.2), the mixture (A.1) is heated to a temperature in the range of from 30 to 150° C., preferably from 40 to 100° C., more preferably from 45 to 90° C.
13. The process of any of embodiments 1 to 12, wherein in (ii), the mixture (A) is treated with the oxygen-containing gas for a period of time in the range of from 0.1 to 240 h, preferably from 0.5 to 160 h, more preferably from 1 to 90 h, preferably by passing the oxygen-containing gas through the mixture (A).
14. The process of any of embodiments 1 to 13, wherein the oxygen-containing gas according to (ii) is selected from the group consisting of oxygen, air, and lean air.
15. The process of any of embodiments 1 to 14, wherein in (iii), the mixture (B) comprises water and is treated with the oxygen-containing gas after work-up, the work-up comprising separating at least a portion of the water from the mixture (B).
16. The process of any of embodiments 1 to 15, wherein in (iii), the mixture (B) is treated with the oxygen-containing gas for a period of time in the range of from 0.1 to 150 h, preferably from 0.5 to 120 h, more preferably from 1 to 90 h, preferably by passing the oxygen-containing gas through the mixture (B).
17. The process of any of embodiments 1 to 16, wherein the oxygen-containing gas according to (iii) is selected from the group consisting of oxygen, air, and lean air.
18. The process of any of embodiments 1 to 17, wherein the mixture B treated in (iii) comprises an inorganic base, preferably selected from the group consisting of potassium hydroxide, sodium hydroxide, and a combination thereof, wherein the inorganic base more preferably comprises, more preferably consists of potassium hydroxide.
19. The process of embodiment 18, wherein the inorganic base is employed at a molar ratio of the inorganic base relative to compound of formula (I) in the range of from 0.1:1 to 1:1, preferably from 0.2:1 to 1:1, more preferably from 0.3:1 to 1:1.
20. The process of any of embodiments 1 to 19, further comprising
(iv) separating the compound of formula (IVa) and/or, preferably and, the compound of formula (IVb) from the mixture (C), obtaining a mixture of which at least 90 weight-%, preferably at least 92 weight-%, more preferably at least 94 weight-%, more preferably at least 96 weight-% consist of the compound of formula (IVa) and/or, preferably and, the compound of formula (IVb).

21. The process of embodiment 20, wherein (iv) comprises
    (iv.1) extracting the mixture (C), preferably with water;
    (iv.2) optionally evaporating the organic solvent, preferably under reduced pressure after extracting the organic phase obtained from (iv.1), preferably with water obtaining a solid;
    (iv.3) dissolving the solid obtained from (iv.2), preferably at a temperature in the range of from 50 to 250° C., more preferably from 60 to 200° C., wherein the organic solvent is preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof, more preferably selected from the group consisting of alcohols, having 1 to 12 carbon atoms;
    (iv.4) cooling the solution obtained from (iv.3), preferably to temperature in the range of from −30 to +25° C., more preferably from −25 to +5° C., obtaining a suspension;
    (iv.5) separating the solid from the suspension obtained from (iv.4);
    (iv.6) preferably drying the solid obtained from (iv.5), preferably under vacuum;
    (iv.7) optionally further purifying the solid obtained from (iv.5) or from (iv.6), preferably from (iv.6), preferably by chromatography.
22. The process of any of embodiments 1 to 19, preferably of embodiment 20, more preferably of embodiment 21, further comprising
    (v) subjecting the mixture obtained from (iii), preferably the mixture obtained from (iv), more preferably the solid obtained from (iv.6), to a hydrogenation reaction, preferably in a solvent, in the presence of a hydrogenation catalyst, obtaining a mixture comprising a compound of formula (Va)

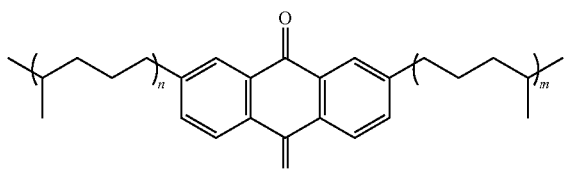

(Va)

and/or, preferably and, a compound of formula (Vb)

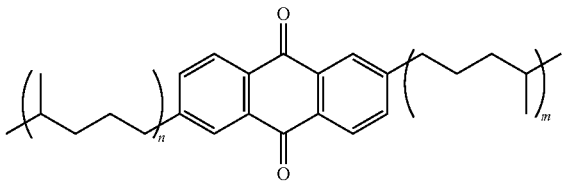

(Vb)

wherein n is 1 or 2 and wherein m is 1 or 2, with n and m preferably both being 1 or both being 2.
23. The process of embodiment 22, wherein the hydrogenation reaction according to (v) is carried out in a solvent, preferably an organic solvent, wherein the solvent is more preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof.
24. The process of embodiment 22 or 23, wherein the hydrogenation catalyst according to (v) comprises one or more metals active in hydrogenation, preferably comprising at least on element selected from the group of transition metals and a combination of two or more thereof, wherein the hydrogenation catalyst more preferably comprises is more preferably selected from the group consisting of Pd, Rh, Ru, Ni, Re, Os, Ir, Pt, Au, Ag, Zr and a combination of two or more thereof wherein the one or more metals more preferably comprise, more preferably consist of, Pd.
25. The process of any of embodiments 22 to 24, wherein the hydrogenation reaction according to (v) is carried out at a temperature in the range of from 20 to 200° C., preferably from 25 to 150° C., more preferably from 30 to 100° C.
26. The process of any of embodiments 22 to 25, wherein the hydrogenation reaction according to (v) is carried out at a hydrogen pressure in the range of from 1 to 50 bar, preferably from 1 to 30 bar, more preferably from 1 to 20 bar, more preferably from 1 to 10 bar.
27. The process of any of embodiments 22 to 26, further comprising crystallizing the compound of formula (Va) and/or, preferably and, formula (Vb) from the mixture obtained in (v).
28. The process of any of embodiments 22 to 26, further comprising
    (vi) treating the mixture obtained in (v) with an inorganic base, preferably selected from the group consisting of potassium hydroxide, sodium hydroxide, and a combination thereof, wherein the inorganic base more preferably comprises, more preferably consists of, potassium hydroxide, obtaining a mixture comprising the compounds of formula (Va) and/or, preferably and, formula (Vb).

29. The process of embodiment 28, wherein the treating according to (vi) is carried out at a temperature in the range of from 30 to 150° C., preferably from 40 to 100° C., more preferably from 45 to 70° C.

30. The process of embodiment 28 or 29, further comprising crystallizing the compound of formula (Va) and/or, preferably and, formula (Vb) from the mixture obtained in (vi).

31. A mixture comprising the compound of formula (Va)

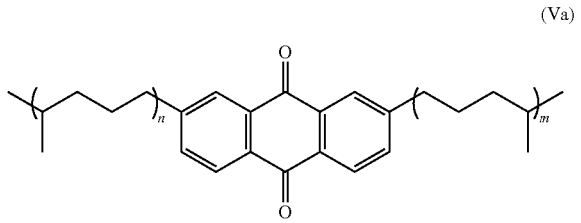
(Va)

and/or, preferably and, formula (Vb)

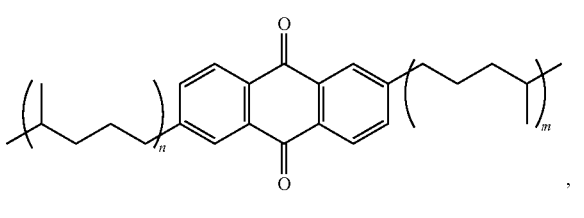
(Vb)

obtainable or obtained by a process according to any of embodiments 22 to 30.

32. A compound of formula (IVa)

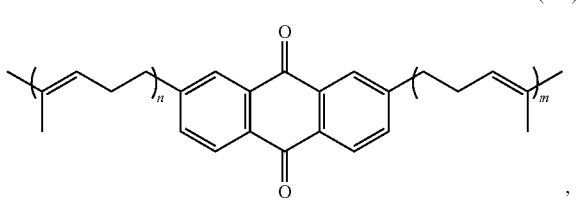
(IVa)

wherein n is 1 and m is 2.

33. A compound of formula (IVb)

(IVb)

wherein n is 1 and m is 2.

34. A compound of formula (Va)

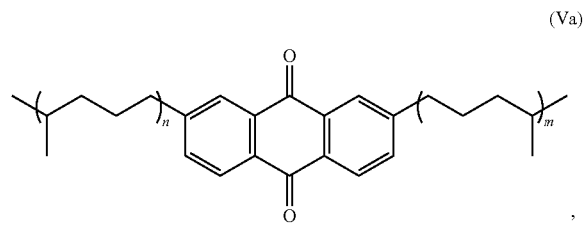
(Va)

wherein n is 1 and m is 2, or wherein n is 1 and m is 1, or wherein n is 2 and m is 2.

35. A compound of formula (Vb)

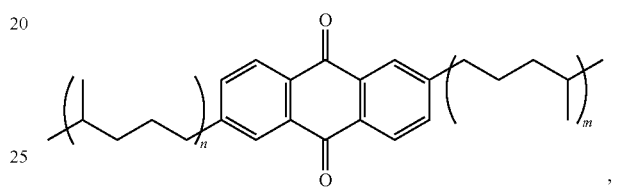
(Vb)

wherein n is 1 and m is 2, or wherein n is 1 and m is 1, or wherein n is 2 and m is 2.

36. A composition comprising a compound of formula (IVa)

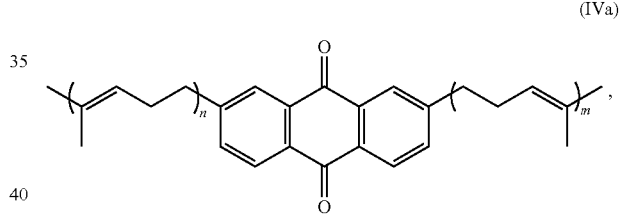
(IVa)

wherein n is 1 or 2 and wherein m is 1 or 2, with n and m preferably both being 1 or both being 2, more preferably both being 1,
and/or, preferably and, a compound of formula (IVb)

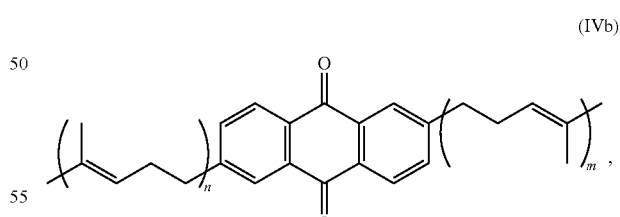
(IVb)

wherein n is 1 or 2 and wherein m is 1 or 2, with n and m preferably both being 1 or both being 2, more preferably both being 1, and wherein at least 95 weight-% of the composition consist of compounds of formula (IVa) and formula (IVb).

37. The composition of embodiment 36, wherein at least 90 weight-%, preferably at least 92 weight-%, more preferably at least 94 weight-%, more preferably at least 96 weight-% of the composition consist of the compounds of formula (IVa) and/or, preferably and formula (IVb).

38. The composition of embodiment 36 or 37, wherein the molar ratio of the compound of formula (IVa) relative to the compound of formula (IVb) is in the range of from 0.2:1 to 5:1, preferably from 0.3:1 to 3:1, more preferably from 0.5:1 to 2:1, more preferably from 0.8:1 to 1.2:1.

39. A composition comprising a compound of formula (Va)

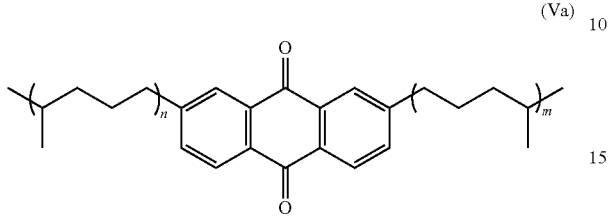

(Va)

wherein n is 1 or 2 and wherein m is 1 or 2, with n and m preferably both being 1 or both being 2, more preferably both being 1, and/or, preferably and, a compound of formula (Vb)

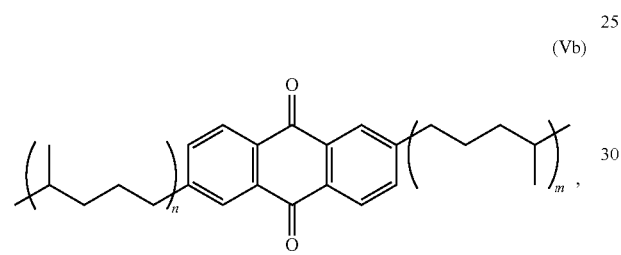

(Vb)

wherein n is 1 or 2 and wherein m is 1 or 2, with n and m preferably both being 1 or both being 2, more preferably both being 1, and wherein at least 95 weight-% of the composition consist of compounds of formula (Va) and formula (Vb).

40. The composition of embodiment 39, wherein at least 90 weight-%, preferably at least 92 weight-%, more preferably at least 94 weight-%, more preferably at least 96 weight-% of the composition consist of the compounds of formula (Va) and/or, preferably and formula (Vb).

41. The composition of embodiment 39 or 40, wherein the molar ratio of the compound of formula (Va) relative to the compound of formula (Vb) is in the range of from 0.2:1 to 5:1, preferably from 0.3:1 to 3:1, more preferably from 0.5:1 to 2:1, more preferably from 0.8:1 to 1.2:1.

42. Use of a compound of formula (IVa)

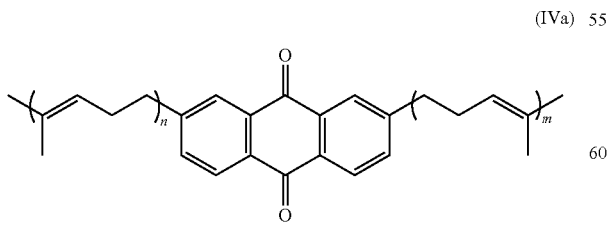

(IVa)

wherein n is 1 and m is 2, or wherein n is 1 and m is 1, or wherein n is 2 and m is 2, or of a compound of formula (IVb)

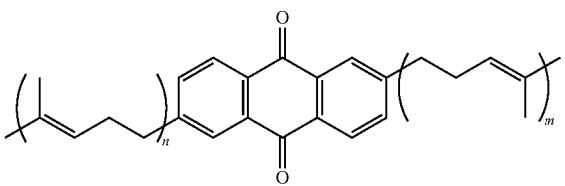

(IVb)

wherein n is 1 and m is 2, or wherein n is 1 and m is 1, or wherein n is 2 and m is 2, or of a composition comprising a compound of formula (IVa) and a compound of formula (IVb), preferably a composition according to any of embodiments 36 to 38, for the preparation of hydrogen peroxide, more preferably as anthraquinone compound in an anthraquinone process for the preparation hydrogen peroxide.

43. Use of a compound of formula (Va)

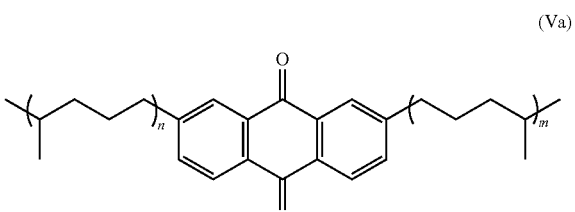

(Va)

wherein n is 1 and m is 2, or wherein n is 1 and m is 1, or wherein n is 2 and m is 2, or of a compound of formula (Vb)

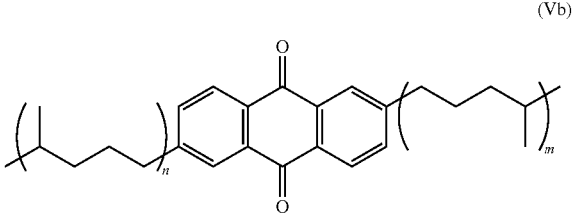

(Vb)

wherein n is 1 and m is 2, or wherein n is 1 and m is 1, or wherein n is 2 and m is 2, or of a composition comprising a compound of formula (Va) and a compound of formula (Vb), preferably a composition according to any of embodiments 39 to 41, for the preparation of hydrogen peroxide, preferably as anthraquinone compound in an anthraquinone process for the preparation hydrogen peroxide.

44. A process for the preparation of hydrogen peroxide, comprising (I) providing a compound of formula (IVa)

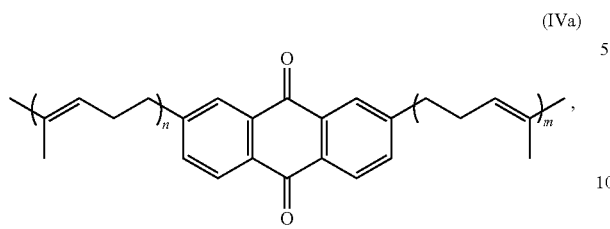

wherein n is 1 and m is 2, or wherein n is 1 and m is 1, or wherein n is 2 and m is 2, or a compound of formula (IVb)

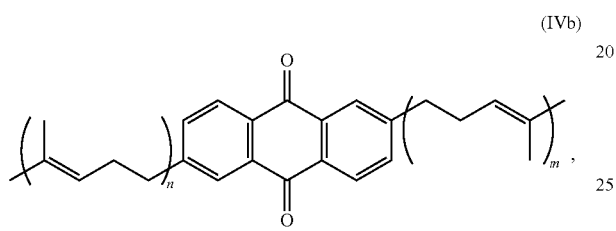

wherein n is 1 and m is 2, or wherein n is 1 and m is 1, or wherein n is 2 and m is 2, or a compound of formula (Va)

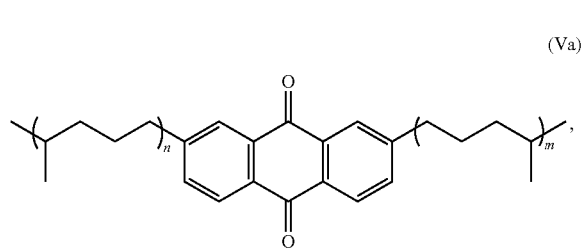

wherein n is 1 and m is 2, or wherein n is 1 and m is 1, or wherein n is 2 and m is 2, or a compound of formula (Vb)

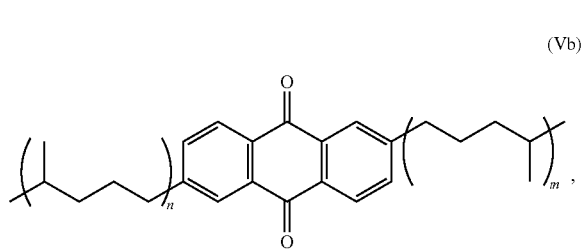

wherein n is 1 and m is 2, or wherein n is 1 and m is 1, or wherein n is 2 and m is 2, or a composition comprising at least one of the compounds of formula (IVa) and (Va) and at least one of the compounds of formula (IVb) and (Vb), preferably a composition comprising a compound of formula (IVa) and a compound of formula (IVb) or a composition comprising a compound of formula (Va) and a compound of formula (Vb), more preferably a composition according to any of embodiments 36 to 38 or a composition according to any of embodiments 39 to 41;

(II) preparing a mixture comprising the compound or the composition, preferably the composition, provided in (I) dissolved in an organic solvent, wherein the solvent is preferably selected from the group consisting of benzene, monoalkylated benzene, for example toluene or tert-butylbenzene, polyalkylated benzene, for example xylene, methylnaphthalene, alkyl phosphates, alkylcyclohexanol esters, N,N-dialkyl carbonamides, N-alkyl carbonamides, N-aryl carbonamides, N,N-dialkyl carbamates, tetraalkyl ureas, cycloalkyl ureas, phenylalkyl ureas, N-alkyl-2-pyrrolidones, N-alkyl caprolactams, alcohols having from 1 to 12 carbon atoms, and a mixture of two or more thereof, more preferably selected from the group consisting of trimethylbenzene, tetramethylbenzene, alkyl phosphates, alcohols having from 1 to 12 carbon atoms such as nonyl alcohols, N,N-dialkyl carbonamides, N,N-dialkyl carbamates, N-alkyl carbonamides, tetraalkyl ureas, cycloalkyl ureas, and a mixture of two or more thereof, and further comprising a hydrogenation catalyst;

(III) subjecting the mixture prepared in (II) to a hydrogenation reaction, obtaining a mixture comprising a compound of formula (VIa)

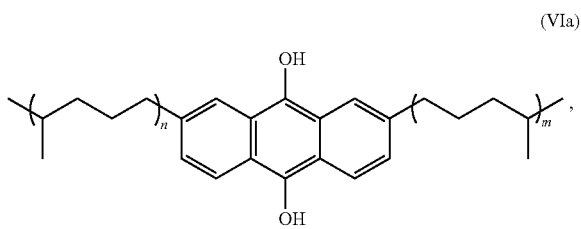

or comprising a compound of formula (VIb)

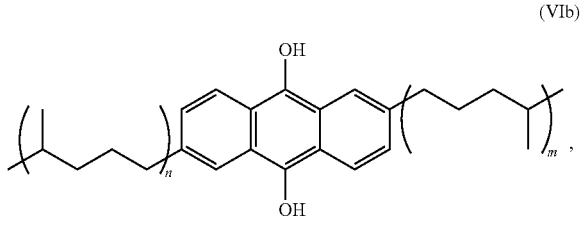

or comprising a compound of formula (VIa) and a compound formula (VIb), preferably comprising a compound of formula (VIa) and a compound of formula (VIb);

(IV) subjecting the mixture obtained in (III) to an oxidation reaction in the presence of an oxygen containing gas, obtaining a mixture comprising the compound of formula (Va), or the compound of formula (Vb), or the compound of formula (Va) and the compound of formula (Vb), preferably comprising the compound of formula (Va) and the compound of formula (Vb), and further comprising hydrogen peroxide;

(V) separating the hydrogen peroxide from the mixture obtained in (IV), obtaining a mixture comprising hydrogen peroxide and a mixture comprising the compound of formula (Va), or the compound of formula (Vb), or the compound of formula (Va) and the compound of formula (Vb), preferably comprising the compound of formula (Va) and the compound of formula (Vb);

(VI) preferably subjecting the mixture obtained in (V), comprising the compound of formula (Va), or the compound of formula (Vb), or the compound of formula (Va) and the compound of formula (Vb), preferably comprising the compound of formula (Va) and the compound of formula (Vb), to at least one repetition of the sequence of steps (III) to (V).

45. The process of embodiment 44, wherein according to (I), the composition comprising a compound of formula (IVa) and a compound of formula (IVb) is provided by a process according to any of claims 1 to 21.

46. The process of embodiment 45, wherein according to (I), the composition comprising a compound of formula (Va) and a compound of formula (Vb) is provided by a process according to any of embodiments 22 to 30.

47. The process of any of embodiments 44 to 46, wherein the hydrogenation catalyst according to (II) comprises a metal active in hydrogenation, preferably palladium, preferably supported on a support preferably comprising at least on element selected from the group consisting of aluminum, barium, calcium, cerium, zirconium and silicon, more preferably comprising at least one compound selected from the group consisting of aluminum oxide, barium sulfate, calcium carbonate, cerium(IV) oxide, silicon oxide and zirconium(IV) oxide.

48. The process of any of embodiments 44 to 47, wherein at least 1 weight-%, more preferably at least 5 weight-%, more preferably at least 10 weight-%, more preferably at least 20 weight-%, more preferably at least 30 weight-% of the mixture comprising hydrogen peroxide obtained according to (V) consist of hydrogen peroxide.

49. A mixture comprising hydrogen peroxide, obtainable or obtained by a process according to any of embodiments 44 to 48, preferably obtainable or obtained in step (V) of the process according to any of embodiments 44 to 48.

50. Use of the mixture according to embodiment 49 for the preparation of propylene oxide, a propylene glycol, a polyol and/or a polyurethane.

The present invention is further illustrated by the following reference examples, examples, and comparative examples.

EXAMPLES

Reference Example 1: IR Measurements

The IR measurements were performed on a Nicolet 6700 spectrometer. The materials were measured as film on a KBr window, wherein in case the materials were present as solid, the solid was solved in dichloromethane prior to applying on the KBr window. The samples were introduced into a high vacuum cell placed into the IR instrument. The spectra were recorded in the range of 4000 $cm^{-1}$ to 400 $cm^{-1}$ at a resolution of 4 $cm^{-1}$. The obtained spectra were represented by a plot having on the x axis the wavenumber ($cm^{-1}$) and on the y axis the absorbance (arbitrary units). For the quantitative determination of the peak heights and the ratio of the peak heights, a baseline correction was carried out.

Reference Example 2: Elemental Analysis

The elemental analysis regarding carbon and hydrogen were performed on an elemental analyzer of model vario Micro cube of the company Elementar, wherein oxygen was used for combustion, and wherein the content of carbon and hydrogen were detected via conductivity measurement.

The elemental analysis regarding oxygen was performed on an elemental analyzer of model EuroVector EA3000 of the firm HEKAtech, wherein soot was used for pyrolysis, and wherein the content of oxygen was detected via conductivity measurement.

The measurements were carried out according to the manufacturer's instructions.

Reference Example 3: GC/MS Measurements

The GC/MS measurements were performed on a gas chromatograph Agilent GC 6890 N using a detector Agilent 5975 MSD and a column Restek 13623.

The measurements were carried out according to the manufacturer's instructions.

Example 1: Preparation of a Mixture of 2,6-bis(4-methylpent-3-enyl)anthracene-9,10-dione and 2,7-bis(4-methylpent-3-enyl)anthracene-9,10-dione (Compounds (IVa) and (IVb) with n,m=1) Starting from 1,4-dihydroxybenzene (Compound (I))

0.19 g copper chloride dihydrate and 0.19 g dry lithium chloride were dissolved in 8 ml distilled water in a round bottom flask, which was equipped with a reflux condensor. 17 ml n-hexanol were added and the obtained solution was heated to an internal temperature of 60° C. 1.55 g 7-methyl-3-methylene-1,6-octadiene and 0.5 g 1,4-dihydroxybenzol were added. Thereafter, technical air was passed through the solution for 96 h, wherein the solution was stirred with a stirring rate of 900 r.p.m. Then, the organic layer was separated, heated to 70° C. and 0.25 g potassium hydroxide were added. Technical air was passed through the thus obtained mixture for 10 h. Thereafter, the obtained mixture was extracted with 30 ml distilled water and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and dried under reduced pressure, wherein a yield to 2,6-bis(4-methylpent-3-enyl)anthracene-9,10-dione and 2,7-bis(4-methylpent-3-enyl)anthracene-9,10-dione of 75% was achieved. The obtained product had a melting point of 69.8° C. and 77.9° C. IR spectrum of the obtained product exhibits the following absorption bands with maximums at (KBr pellet): 462 $cm^{-1}$, 550 $cm^{-1}$, 621 $cm^{-1}$, 666 $cm^{-1}$, 718 $cm^{-1}$, 743 $cm^{-1}$, 833 $cm^{-1}$, 848 $cm^{-1}$, 879 $cm^{-1}$, 932 $cm^{-1}$, 970 $cm^{-1}$, 1151 $cm^{-1}$, 1104 $cm^{-1}$, 1221 $cm^{-1}$, 1258 $cm^{-1}$, 1300 $cm^{-1}$, 1325 $cm^{-1}$, 1383 $cm^{-1}$, 1439 $cm^{-1}$, 1574 $cm^{-1}$, 1596 $cm^{-1}$, 1673 $cm^{-1}$, 2858 $cm^{-1}$, 2919 $cm^{-1}$, 2963 $cm^{-1}$, 3029 $cm^{-1}$, 3054 $cm^{-1}$, 3433 $cm^{-1}$. Further, the following data were found by mass spectrometry (GC/MS) and elemental analysis (EA): GC/MS: $O_{26}H_{28}O_2$ calculated (m/z): 372.21 determined (m/z)): 372; EA: $C_{26}H_{28}O_2$ calculated: C: 83.83 weight-%, H: 7.58 weight-%, O: 8.59 weight-% determined: C: 82.9 weight-%, H: 7.6 weight-%, O: 8.8 weight-%.

Results of Example 1

Example 1 shows that 2,6-bis(4-methylpent-3-enyl)anthracene-9,10-dione and 2,7-bis(4-methylpent-3-enyl)anthracene-9,10-dione may be obtained in a one-pot process starting from 1,4-dihydroxybenzene, wherein a combination of copper chloride and lithium chloride is used as catalyst.

Example 2: Preparation of a Mixture of 2,6-bis(4,8-dimethylnonan-3,7-dienyl)anthracene-9,10-dione and 2,7-bis(4,8-dimethylnonan-3,7-dienyl)anthracene-9,10-dione (Compounds (Iva) and (IVb) with n,m=2) Starting from 1,4-dihydroxybenzene (Compound (I))

0.19 g copper chloride dihydrate and 0.19 g dry lithium chloride were dissolved in 8 ml distilled water in a round bottom flask, which was equipped with a reflux condensor. 17 ml n-hexanol were added and the obtained solution was heated to an internal temperature of 60° C. 3.00 g (6E)-7,11-dimethyl-3-methylene-1,6,10-dodecatrinen and 0.5 g 1,4-dihydroxybenzol were added. Thereafter, technical air was passed through the solution for 96 h, wherein the solution was stirred with a stirring rate of 900 r.p.m. Then, the organic layer was separated, heated to 70° C. and 0.25 g potassium hydroxide were added. Technical air was passed through the thus obtained mixture for 10 h. Thereafter, the obtained mixture was extracted with 30 ml distilled water and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and dried under reduced pressure. Yield: 69% of 2,6-bis(4,8-dimethylnonan-3,7-dienyl)anthracene-9,10-dione and 1.11 g 2,7-bis(4,8-dimethylnonan-3,7-dienyl)anthracene-9,10-dione were obtained. 2,6-bis(4,8-dimethylnonan-3,7-dienyl)anthracene-9,10-dione had a melting point of 82.4° C. IR spectrum of the obtained product exhibits the following absorption bands with maximums at (KBr pellet): 414 $cm^{-1}$, 452 $cm^{-1}$, 596 $cm^{-1}$, 618 $cm^{-1}$, 653 $cm^{-1}$, 718 $cm^{-1}$, 726 $cm^{-1}$, 750 $cm^{-1}$, 807 $cm^{-1}$, 881 $cm^{-1}$, 852 $cm^{-1}$, 918 $cm^{-1}$, 973 $cm^{-1}$, 1110 $cm^{-1}$, 1147 $cm^{-1}$, 1212 $cm^{-1}$, 1262 $cm^{-1}$, 1298 $cm^{-1}$, 1324 $cm^{-1}$, 1383 $cm^{-1}$, 1451 $cm^{-1}$, 1594 $cm^{-1}$, 1670 $cm^{-1}$, 2853 $cm^{-1}$, 2913 $cm^{-1}$, 2968 $cm^{-1}$, 3442 $cm^{-1}$. Further, the following data were found by mass spectrometry (GC/MS) and elemental analysis (EA): GC/MS: $C_{36}H_{44}O_2$ calculated (m/z): 508.33, determined (m/z): 508; EA of 2,6-bis(4,8-dimethylnonan-3,7-dienyl)anthracene-9,10-dione $C_{36}H_{44}O_2$ calculated: C: 84.99 weight-%, H: 8.72 weight-%, O: 6.29 weight-%; determined: C: 83.1 weight-%, H: 8.6 weight-%, O: 7.8 weight-%.

Results of Example 2

Example 2 shows that 2,6-bis(4,8-dimethylnonan-3,7-dienyl)anthracene-9,10-dione and 2,7-bis(4,8-dimethylnonan-3,7-dienyl)anthracene-9,10-dione may be obtained in a one-pot process starting from 1,4-dihydroxybenzene, wherein a combination of copper chloride and lithium chloride is used as catalyst.

Example 3: Preparation of a Mixture of 2-(4,8-dimethylnonan-3,7-dienyl)-6-(4-methylpent-3-enyl)-anthracene-9,10-dione and 2-(4,8-dimethylnonan-3,7-dienyl)-7-(4-methylpent-3-enyl)-anthracene-9,10-dione (Compounds (IVa) and (IVb) with n=1, m=2) Starting from 1,4-dihydroxybenzene (Compound (I))

0.19 g copper chloride dihydrate and 0.19 g dry lithium chloride were dissolved in 8 ml distilled water in a round bottom flask, which was equipped with a reflux condensor. 17 ml n-hexanol were added and the obtained solution was heated to an internal temperature of 60° C. 0.77 g 7-methyl-3-methylene-1,6-octadiene and 0.5 g 1,4-dihydroxybenzol were added. Thereafter, technical air was passed through the solution for 96 h, wherein the solution was stirred with a stirring rate of 900 r.p.m. The reaction was monitored by online-GC/MS measurements. After the 1,4-dihydroxybenzene was consumed, 1.50 g (6E)-7,11-dimethyl-3-methylene-1,6,10-dodecatrinen was added and the reaction was stirred under said conditions for another 96 h. Then, the organic layer was separated, heated to 70° C. and 0.25 g potassium hydroxide were added. Technical air was passed through the thus obtained mixture for 10 h. Thereafter, the obtained mixture was extracted with 30 ml distilled water and dried over $Na_2SO_4$. The solvent in the solution was evaporated under reduced pressure. Yield: 71% of 2-(4,8-dimethylnonan-3,7-dienyl)-6-(4-methylpent-3-enyl)-anthracene-9,10-dione and 2-(4,8-dimethylnonan-3,7-dienyl)-7-(4-methylpent-3-enyl)-anthracene-9,10-dione were obtained as dark yellow oil. IR spectrum of the obtained product exhibits the following absorption bands with maximums at (KBr pellet): 410 $cm^{-1}$, 461 $cm^{-1}$, 618 $cm^{-1}$, 657 $cm^{-1}$, 724 $cm^{-1}$, 726 $cm^{-1}$, 744 $cm^{-1}$, 821 $cm^{-1}$, 865 $cm^{-1}$, 867 $cm^{-1}$, 973 $cm^{-1}$, 1112 $cm^{-1}$, 1149 $cm^{-1}$, 1199 $cm^{-1}$, 1254 $cm^{-1}$, 1299 $cm^{-1}$, 1322 $cm^{-1}$, 1381 $cm^{-1}$, 1447 $cm^{-1}$, 1583 $cm^{-1}$, 1664 $cm^{-1}$, 2853 $cm^{-1}$, 2968 $cm^{-1}$, 3453 $cm^{-1}$. Further, the following data were found by mass spectrometry (GC/MS) and elemental analysis (EA): GC/MS: $O_{31}H_{36}O_2$ calculated (m/z): 440,62, determined (m/z): 440; EA of 2,6-bis(4,8-dimethylnonan-3,7-dienyl)anthracene-9,10-dione $O_{31}H_{36}O_2$ calculated: C: 84.50 weight-%, H: 8.24 weight-%, O: 7.26 weight-%; determined: C: 84.00 weight-%, H: 8.9 weight-%, O: 7.5 weight-%.

Results of Example 3

Example 3 shows that 2-(4,8-dimethylnonan-3,7-dienyl)-6-(4-methylpent-3-enyl)-anthracene-9,10-dione and 2-(4,8-dimethylnonan-3,7-dienyl)-7-(4-methylpent-3-enyl)-anthracene-9,10-dione may be obtained in a one-pot process starting from 1,4-dihydroxybenzene, wherein a combination of copper chloride and lithium chloride is used as catalyst.

Example 4: Preparation of a Mixture of 2,6-diisohexylanthracene-9,10-dione and 2,7-diisohexylanthracene-9,10-dione (Compounds (IVa) and (IVb) with n,m=1) by Use of a Palladium Catalyst on Carbon A solution of 2.25 g of the product obtained in Example 1 dissolved in 150 ml ethanol was provided in an autoclave. 0.65 g of a palladium catalyst on carbon (5% Pd/C) were added. The autoclave was closed and flushed with 10 bar nitrogen for five times. The solution was cooled by air cooling having 20° C. and the solution was stirred with a stirring rate of 700 r.p.m. Thereafter, the pressure was set to 3.0 bar by introducing hydrogen gas. The pressure decreased within approximately 2 h to 1 bar and thereafter, the pressure was again set to 3 bar by introducing hydrogen gas. After approximately 5 h the pressure decreased to 1 bar and stirring was stopped. The pressure was set to atmosphere pressure and the autoclave was flushed with 10 bar nitrogen for two times. The palladium catalyst was filtered off and the solvent of the obtained solution was evaporated under reduced pressure, so that a solid was obtained. Boiling ethanol was then added until the solid was dissolved completely. The solution was cooled to 22° C. and then further cooled to −22° C. for 24 h. The obtained solid was filtered off from the mother liquor and dried under reduced pressure. The solvent in the mother liquor was evaporated and the thus obtained solid was purified as described above.

2.07 g (95%) a mixture of 2,6-diisohexylanthracene-9,10-dione and 2,7-diisohexylanthracene-9,10-dione were obtained. The obtained product had a melting point of 79.1° C. The IR spectrum of the obtained product exhibits the following absorption bands with maximums at (KBr pellet): 413 $cm^{-1}$, 553 $cm^{-1}$, 615 $cm^{-1}$, 654 $cm^{-1}$, 720 $cm^{-1}$, 750 $cm^{-1}$, 848 $cm^{-1}$, 879 $cm^{-1}$, 917 $cm^{-1}$, 934 $cm^{-1}$, 983 $cm^{-1}$, 1144 $cm^{-1}$, 1169 $cm^{-1}$, 1211 $cm^{-1}$, 1297 $cm^{-1}$, 1308 $cm^{-1}$, 1328 $cm^{-1}$, 1365 $cm^{-1}$, 1383 $cm^{-1}$, 1459 $cm^{-1}$, 1470 $cm^{-1}$, 1596 $cm^{-1}$, 1673 $cm^{-1}$, 2867 $cm^{-1}$, 2926 $cm^{-1}$, 2951 $cm^{-1}$, 3066 $cm^{-1}$, 3477 $cm^{-1}$. Further, the following data were found by mass spectrometry (GC/MS) and elemental analysis (EA): GC/MS: $C_{26}H_{32}O_2$ calculated (m/z): 376.24; determined (m/z): 376; EA: $C_{26}H_{32}O_2$ calculated: C: 82.94, H: 8.57, O: 8.50 determined: C: 82.3, H: 8.6, O: 8.9.

Results of Example 4

Example 4 shows that 2,6-diisohexylanthracene-9,10-dione and 2,7-diisohexylanthracene-9,10-dione are obtained by a process according to the present invention in an overall yield of 68%.

Example 5: Preparation of a Mixture of 2,6-diisohexylanthracene-9,10-dione and 2,7-diisohexylanthracene-9,10-dione (Compounds (IVa) and (IVb) with n,m=1) by Use of Different Catalysts and Solvents 200 mg of the mixture obtained in Example 1, catalyst (the amount used is given in Table 1 below) and 5 ml solvent (the solvent used is given in Table 1 below) were provided in an autoclave having a nominal volume of 80 ml. The pressure was set to 20.0 bar by introducing hydrogen gas and the reaction mixture was stirred for 15 h at 40° C. Thereafter, the catalyst was separated by filtration and the solvent was evaporated under reduced pressure.

Example 6: Preparation of a Mixture of 2,6-(1,5-dimethy)-nonylanthracene-9,10-dione and 2,7-(1,5-dimethy)-nonylanthracene-9,10-dione (Compounds (IVa) and (IVb) with n,m=2)

3.0 g of the mixture obtained in Comparative Example 2, 0.32 g $Rh(COD)_2BF_4$ and 100 ml Methanol were provided in an autoclave having a nominal volume of 300 ml. The pressure was set to 20.0 bar by introducing hydrogen gas and the reaction mixture was stirred for 48 h at 40° C. Thereafter, the catalyst was separated by filtration and the solvent was evaporated under reduced pressure.

2.1 g (70%) of a mixture of 2,6-diisohexylanthracene-9,10-dione and 2,7-diisohexylanthracene-9,10-dione were obtained in form of a wax. IR spectrum of the obtained mixture exhibits the following absorption bands with maximums at (KBr pellet): 415 $cm^{-1}$, 556 $cm^{-1}$, 623 $cm^{-1}$, 655 $cm^{-1}$, 751 $cm^{-1}$, 879 $cm^{-1}$, 934 $cm^{-1}$, 983 $cm^{-1}$, 1146 $cm^{-1}$, 1171 $cm^{-1}$, 1211 $cm^{-1}$, 1308 $cm^{-1}$, 1328 $cm^{-1}$, 1365 $cm^{-1}$, 1459 $cm^{-1}$, 1470 $cm^{-1}$, 1675 $cm^{-1}$, 2867 $cm^{-1}$, 2951 $cm^{-1}$, 3066 $cm^{-1}$, 3469 $cm^{-1}$. Further, the following data were found by mass spectrometry (GC/MS) and elemental analysis (EA): GC/MS: $C_{26}H_{32}O_2$ calculated (m/z): 516.40; determined (m/z): 516; EA: $C_{26}H_{32}O_2$ calculated: C: 83.67 weight-%, H: 10.14 weight-%, O: 6.19 weight-%; determined: C: 83.75 weight-%, H: 10.22 weight-%, O: 6.03 weight-%.

Results of Example 6

Example 6 shows that a mixture of 2,6-(1,5-dimethy)-nonylanthracene-9,10-dione and 2,7-(1,5-dimethy)-nonylanthracene-9,10-dione can be obtained by one of the hydrogenation procedures mentioned in Example 5.

Example 7: Preparation of a Mixture of 2,6-diisohexylanthracene-9,10-dione and 2,7-diisohexylanthracene-9,10-dione (Compounds (IVa) and (IVb) with n,m=1) and Subsequent Treatment with KOH 15 g of the mixture obtained in Example 2, 2.5 g of a palladium catalyst on carbon (5% Pd/C) and 200 ml ethanol

TABLE 1

| Complex | Ligand | Additive | Solvent | Conversion (starting material) | Selectivity (to product) |
|---|---|---|---|---|---|
| 10 mol-% $[Rh(COD)_2][BF_4]^-$ [(1)] | 10 mol-% DTBPP [(2)] | — | MeOH | 100% | 75% |
| 17 mol % $[Ru(COD)Cl_2]_n$ [(1)] | 10 mol-% $PCy_3$ [(3)] | 35 mol % BMIMCl [(4)] | THF | 100% | 60% |
| 1 mol-% 2% Pd/C | — | — | MeOH | 100% | 29% |
| 1 mol-% 2% Pd/C | — | — | toluene | 100% | 18% |

[(1)] COD = 1,5-cyclooctadiene
[(2)] DTBPP = 1,2-Bis(diter-butyl-phosphinomethyl)benzol
[(3)] $PCy_3$ = tricyclohexylphosphin
[(4)] BMIMCl = 1-butyl-3-methylimidazolium chloride Results of Example 5

Example 5 shows that a variety of homogeneous and heterogeneous catalysts and solvents may be used to hydrogenate 2,6-bis(4-methylpent-3-enyl)anthracene-9,10-dione and 2,7-bis(4-methylpent-3-enyl)anthracene-9,10-dione even at an absolute hydrogen pressure of 20 bar.

were provided in an autoclave. The autoclave was closed and flushed with 1 bar nitrogen for three times. The pressure was set to 1.5 bar by introducing hydrogen gas and the reaction mixture was stirred for 140 h at 25° C. Thereafter, the catalyst was separated by filtration and the solvent was evaporated under reduced pressure. The resulting reaction mixture was analyzed by GC-MS. The conversion of the starting material was 100% and the selectivity to 2,6- diisohexylanthracene-9,10-dione and 2,7-diisohexylanthracene-9,10-dione was 81%, the rest being over-hydrogenated byproducts The resulting solution was heated to an internal temperature of 60° C. and 3.8 g KOH were added. After KOH was solved in the solution, technical air containing 4 volume-% oxygen, was passed through the solution with a flow rate of 10 l/h for a period of 4 h and with a stirring rate of 750 r.p.m. The obtained solution was extracted with 70 ml distilled water for two times. The organic layer was separated and dried over $Na_2SO_4$. The solvent in the solution was evaporated under reduced pressure, so that a solid was obtained. Boiling ethanol was then added until the solid was dissolved completely. The solution was cooled to 22° C. and then further cooled to −22° C. for 15 h. The obtained solid was filtered off from the mother liquor and washed with ethanol having a temperature of −22° C. until the solid was colorless. The obtained product was dried under reduced pressure. The solvent in the mother liquor was evaporated and the thus obtained solid was purified as described above.

The resulting reaction mixture was analyzed by GC-MS, wherein the selectivity to 2,6-diisohexylanthracene-9,10-dione and 2,7-diisohexylanthracene-9,10-dione was 97%.

Results of Example 7

Example 7 shows that a subsequent treatment with potassium hydroxide leads to an increased selectivity to 2,6-diisohexylanthracene-9,10-dione and 2,7-diisohexylanthracene-9,10-dione. Without the treatment with potassium hydroxide, a selectivity to 2,6-diisohexylanthracene-9,10-dione and 2,7-diisohexylanthracene-9,10-dione of 81% is achieved, wherein the subsequent treatment with potassium hydroxide increases the selectivity to 97%. This can be explained by the re-oxidation of the over-hydrogenated byproducts that are generated in the hydrogenation step even under such mild conditions described.

Example 8: Preparation of a Mixture of 2,6-bis(4-methylpent-3-enyl)-1,4,4a,5,8,8a,9a,10a-octahydroanthracene-9-10-dione and 2,7-bis(4-methyl pent-3-enyl)-1,4,4a,5,8,8a,9a,10a-octahydroanthracene-9-10-dione (Compounds (IVa) and (IVb) with n,m=1) Starting from 1,4-dihydroxybenzene (Compound (I))

0.49 g of a catalyst consisting of 60 weight-% copper(II) oxide, 20 weight-% zinc(II) oxide, 17.5 weight-% aluminum (III) oxide, 2.5 weight-% zirconium (IV) oxide were suspended in a mixture of 15 mL distilled water and 30 mL of 2-ethylhexanol. The obtained suspension was heated to an internal temperature of 60° C. and 4.65 g 7-methyl-3-methylene-1,6-octadiene and 1.5 g 1,4-dihydroxybenzol were added to the suspension. Thereafter, technical air was passed through the solution for 72 h, wherein the solution was stirred. The resulting reaction mixture was cooled to 22° C. and the organic layer was separated, dried over $Na_2SO_4$ and the solvent was evaporated under reduced pressure. The obtained solid was recrystallized in ethanol, wherein 5.18 g (Yield: 84%) of 2,6-bis(4-methylpent-3-enyl)-1,4,4a,5,8,8a,9a,10a-octahydroanthracene-9-10-dione and 2,7-bis(4-methyl-pent-3-enyl)-1,4,4a,5,8,8a,9a,10a-octahydroanthracene-9-10-dione were obtained. The product obtained was further treated with KOH in the presence of an oxygen containing gas according to Example 2 to obtain 2,6-bis(4-methylpent-3-enyl)anthracene-9,10-dione and 2,6-bis(4-methylpent-3-enyl)anthracene-9,10-dione.

Results of Example 8

Example 8 shows that 2,6-bis(4-methylpent-3-enyl)-1,4,4a,5,8,8a,9a,10a-octahydroanthracene-9-10-dione and 2,7-bis(4-methylpent-3-enyl)-1,4,4a,5,8,8a,9a,10a-octahydroanthracene-9-10-dione and further 2,6-bis(4-methylpent-3-enyl)anthracene-9,10-dione and 2,7-bis(4-methylpent-3-enyl)anthracene-9,10-dione may be obtained by use of different catalyst and solvents, starting from 1,4-dihydroxybenzene, wherein 2-ethylhexanol and an heterogeneous catalyst containing copper, zinc, aluminum and zirconium is used.

Example 9: Preparation of a Mixture of 2,6-bis(4-methylpent-3-enyl)anthracene-9,10-dione and 2,7-bis(4-methylpent-3-enyl)anthracene-9,10-dione (Compounds (IVa) and (IVb) with n,m=1) Starting from 1,4-dihydroxybenzene (Compound (I))

0.49 g of a catalyst consisting of 60 weight-% copper(II) oxide, 20 weight-% zinc(II) oxide, 17.5 weight-% aluminum (III) oxide, 2.5 weight-% zirconium (IV) oxide were suspended in a mixture of 15 mL distilled water and 30 mL of 2-ethylhexanol. The obtained suspension was heated to an internal temperature of 60° C. 4.65 g 7-methyl-3-methylene-1,6-octadiene and 1.5 g 1,4-dihydroxybenzol were added to the suspension. Thereafter, technical air was passed through the solution for 240 h, wherein the solution was stirred. The resulting reaction mixture was cooled to 22° C. and the organic layer was separated, dried over $Na_2SO_4$ and the solvent was evaporated under reduced pressure. The obtained solid was recrystallized in ethanol, wherein 4.51 g of 2,6-bis(4-methylpent-3-enyl)anthracene-9,10-dione and 2,7-bis(4-methylpent-3-enyl)anthracene-9,10-dione starting from benzene-1,4-diol were obtained.

Results of Example 8 and 9

Comparison of Example 8 with Example 9 shows that an extension of the reaction time leads to an oxidation of 2,6-bis(4-methylpent-3-enyl)-1,4,4a,5,8,8a,9a,10a-octa-hydro-anthracene-9-10-dione and 2,7-bis(4-methylpent-3-enyl)-1,4,4a,5,8,8a,9a,10a-octahydroanthra-cene-9-10-dione by the technical air used, wherein 2,6-bis(4-methylpent-3-enyl)anthracene-9,10-dione and 2,7-bis(4-methylpent-3-enyl)anthracene-9,10-dione starting from benzene-1,4-diol are obtained without the use of an additional catalyst.

Comparative Example 1: Preparation of 2-(3-methylbut-2-en-1-yl)anthracene-9,10-dione 2-(3-methylbut-2-en-1-yl-anthracene-9,10-dione was prepared according to Example 8 in EP 1 178 032 A1: 850 g naphthoquinine were added to a mixture of 4 l toluene and 1.3 l n-butane and the obtained mixture was heated to 90° C. Thereafter, 990 g myrcene were added and after 5 h the mixture was cooled to 70° C. 250 ml water, 52 ml 50% NaOH and 50 ml diethyl amine were added and the resulting mixture was purged by oxygen gas at 70° C. for a period of 5 h. The aqueous layer was separated and the organic layer was washed with diluted phosphoric acid. The solvent in the organic layer was evaporated under reduced pressure and the crude product was purified by crystallization.

Comparative Example 2: Preparation of 2,3,6,7-tetramethyl-1,4,4a,5,8,8a,9a,10a-octahydroanthracene-9,10-dione 10.0 g cyclohexa-2,5-diene-1,4-dione were suspended in 30 ml of a mixture of toluene and n-butanol having a volume ratio of 3:1. This suspension and 10.26 g 2,3-dimethylbuta-1,3-diene were provided in an autoclave having a nominal volume of 100 ml and the obtained mixture was heated to an internal temperature of 90° C. and stirred for 2 days at this temperature. Thereafter, the mixture was cooled to 22° C. and filtered. The thus obtained solution was used for the preparation of 2,3,6,7-tetramethylanthracene-9,10-dione without further purification.

Comparative Example 3: Preparation of 2,3,6,7-tetramethylanthracene-9,10-dione The solution obtained in Comparative Example 2 was set to a temperature of 60° C. and then 5.13 g KOH were added. After KOH was dissolved completely, compressed air was passed through the solution for a period of 5 h with a stirring rate of 700 r.p.m. Thereafter, the mixture was cooled to 22° C. and the solid thus created was separated by filtration and washed with cooled dichloromethane and water. The obtained solid was dried for 24 h at 70° C. in vacuum.

IR spectrum of the obtained mixture exhibits the following absorption bands with maximums at (KBr pellet): 412 $cm^{-1}$, 542 $cm^{-1}$, 655 $cm^{-1}$, 743 $cm^{-1}$, 872 $cm^{-1}$, 934 $cm^{-1}$, 1146 $cm^{-1}$, 1170 $cm^{-1}$, 1211 $cm^{-1}$, 1308 $cm^{-1}$, 1328 $cm^{-1}$, 1365 $cm^{-1}$, 1459 $cm^{-1}$, 1470 $cm^{-1}$, 1684 $cm^{-1}$, 2867 $cm^{-1}$, 3123 $cm^{-1}$, 3415 $cm^{-1}$. Further, the following data were found by mass spectrometry (GC/MS) and elemental analysis (EA): GC/MS: $C_{18}H_{16}O_2$ calculated (m/z): 264.12; determined (m/z): 264; EA: $C_{18}H_{16}O_2$ calculated: C: 81.79 weight-%, H: 6.10 weight-%, O: 12.11 weight-%; determined: C: 81.53 weight-%, H: 6.05 weight-%, O: 12.42 weight-%.

Example 10: Determination of the Solubility 0.06 ml of a mixture of xylene (50 volume-%) and diisobutylcarbinol (50 volume-%) were added to 1 g of the respective anthraquinone derivative at 22° C. every 60 seconds until the anthraquinone derivative was dissolved completely. The results of the solubility test are shown in Table 2 below.

Results of Example 10

As may be taken from the solubility test of the different anthraquinone derivatives, the anthraquinone derivatives having small substituents are insoluble (anthraquinone derivative obtained from Comparative Example 3) or only poorly soluble (commercially available anthraquinone derivative) in the used solvent system compared to the anthraquinone derivatives having 2 substituents, wherein these substituents have six or eleven carbon atoms. However, the preferred anthraquinone derivative according to the present invention, which is obtained from Example 4 exhibits the highest solubility in the solvent system used.

Example 11: Preparation of Hydrogen Peroxide by Use of Anthraquinone Derivatives 5 g of the anthraquinone derivative obtained from Example 4 were dissolved in an equivolume mixture of xylene and diisobutylcarbinol at 30° C. to obtain 100 ml of an anthraquinone solution. 2 g of a palladium catalyst on alumina was added to 50 ml of the anthraquinone solution and then the solution was made to absorb the theoretical amount of hydrogen at 30° C. The obtained solution has been left untouched for 15 h to thoroughly precipitate the excess of anthrahydroquinone. After the catalyst and the precipitate have been separated by filtration under a current of nitrogen, the resulting solution was stirred under air in order to oxidize the anthrahydroquinone back to the corresponding anthraquinone. The produced hydrogen peroxide was extracted with water. After the extraction of the hydrogen peroxide was completed, 25 mL of the working solution were further submitted to subsequent hydrogenation at 30° C. as described above until a state of saturation was reached. The amount of absorbed hydrogen until the precipitation of the anthrahydroquinone that was observed corresponded to a solubility of the anthrahydroquinone obtained from the anthraquinone described in Example 4 in said equivolume mixture of xylene and diisobutylcarbinol of 1.01 mol/l.

TABLE 2

| Obtained from | Anthraquinone derivative | Solubility [mol/l] |
| --- | --- | --- |
| Example 1 | 2,7-bis(4-methylpent-3-enyl)anthracene-9,10-dione and 2,6-bis(4-methylpent-3-enyl)anthracene-9,10-dione | 0.77 |
| Example 4 | 2,7-diisohexylanthracene-9,10-dione and 2,6-diisohexylanthracene-9,10-dione | 1.61 |
| Example 2 | 2,6-bis(4,8-dimethylnonan-3,7-dienyl)anthracene-9,10-dione and 2,7-bis(4,8-dimethylnonan-3,7-dienyl)anthracene-9,10-dione | 0.65 |
| Example 6 | 2,6-(1,5-dimethy)-nonylanthracene-9,10-dione and 2,7-(1,5-dimethy)-nonylanthracene-9,10-dione | 0.39 |
| Comparative Example 1 | 2-(3-methylbut-2-en-1-yl)-anthracene-9,10-dione | 0.77 |
| Comparative Example 3 | 2,3,6,7-tetramethylanthracene-9,10-dione | Insoluble |
| (commercially available) | 2-ethylanthraquinone | 0.27 |

Results of Example 10

TABLE 3

| Alkylanthrahydroquinone obtained from | Anthraquinone derivative | Solubility [mol/l] | Yield of hydrogen peroxide [g/l] |
|---|---|---|---|
| Example 4 | 2,7-diisohexylanthracene-9,10-dione and 2,6-diisohexylanthracene-9,10-dione ((IVa) and (IVb)) | 1.01 | 32.4 |

SUMMARY OF THE EXAMPLES

As shown in Examples 1 to 8, 2,6-diisohexylanthracene-9,10-dione and 2,7-diisohexylanthracene-9,10-dione may be obtained by a sustainable and atom efficient process according to the present invention. Further, Example 9 shows 2,6-diisohexylanthracene-9,10-dione and 2,7-diisohexylanthracene-9,10-dione according to the present invention exhibit the advantage that these compound have the highest solubility in the solvent system used when compared to the anthraquinone derivatives obtained according to the Comparative Examples.

CITED LITERATURE

Ullmann's Encyclopedia of Industrial Chemistry, Vol. 18, chapter "Hydrogen Peroxide", DOI: 10.1002/14356007.a13_443.pub2.
GB 1 387 511 A1
GB 1 387 512
DE 43 39 649 A1
DE 1 051 257

The invention claimed is:

1. A process for the preparation of an anthraquinone derivative, the process comprising:
(i) providing a mixture (A) comprising: a compound of formula (I)

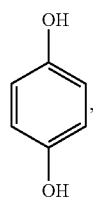

(I), a compound of formula (II)

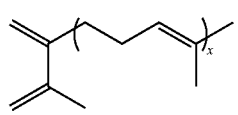

(II)

wherein x is 1, or a compound of formula (II) wherein x is 2, or a mixture of a compound of formula (II) wherein x is 1 and a compound of formula (II) wherein x is 2, a dehydrogenation catalyst, and a liquid solvent system;

(ii) treating the mixture (A) with an oxygen-containing gas obtaining a mixture (B) comprising a compound of formula (IIIa)

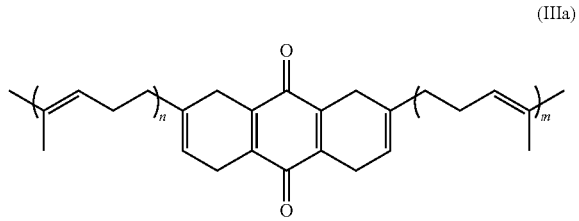

(IIIa)

and/or, a compound of formula (IIIb)

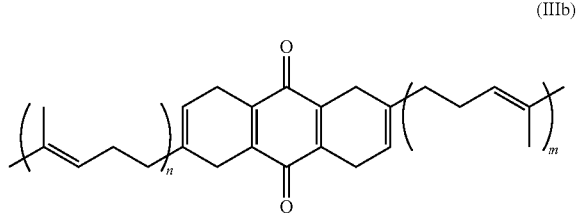

(IIIb)

wherein, in each of formula (IIIa) and (IIIb), n is 1 or 2 and wherein, in each of formula (IIIa) and (IIIb), m is 1 or 2; and (iii) treating the mixture (B), optionally after work-up, with an oxygen-containing gas, obtaining a mixture (C) comprising a compound of formula (IVa)

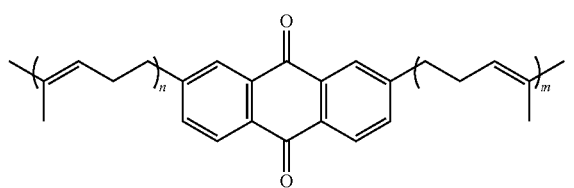

(IVa)

and/or a compound of formula (IVb)

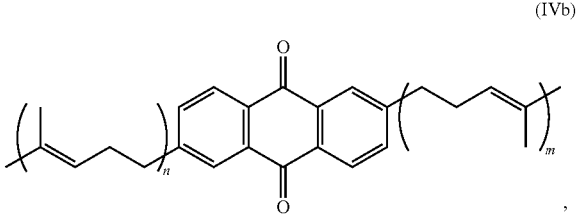

(IVb)

, wherein, in each of formula (IVa) and (IVb), n is 1 or 2 and wherein, in each of formula (IVa) and (IVb), m is 1 or 2.

2. The process of claim 1, wherein the mixture (A) provided in (i) comprises a compound of formula (II) wherein x is 1 and the mixture (B) obtained in (ii) comprises a compound of formula (IIIa) and a compound of formula (IIIb) wherein n is 1 and m is 1, and the mixture (C) obtained in (iii) comprises a compound of formula (IVa) and a compound of formula (IVb) wherein n is 1 and m is 1; or wherein the mixture (A) provided in (i) comprises a compound of formula (II) wherein x is 2 and the mixture (B) obtained in (ii) comprises a compound of formula (IIIa) and a compound of formula (IIIb) wherein n is 2 and m is 2, and the mixture (C) obtained in (iii) comprises a compound of formula (IVa) and a compound of formula (IVb) wherein n is 2 and m is 2.

3. The process of claim 1, wherein the sequence of (i) to (iii) is carried out as a one-pot process.

4. The process of claim 1, wherein the dehydrogenation catalyst according to (i) comprises at least one element selected from the group consisting of palladium, platinum, copper, lithium, zinc, zirconium, and aluminum.

5. The process of claim 1, wherein said providing the mixture (A) according to (i) comprises admixing the compound of formula (I) with the compound of formula (II) at a molar ratio of the compound of formula (I) relative to the compound of formula (II) in the range of from 0.1:1 to 0.5:1.

6. The process of claim 1, wherein the liquid solvent system according to (i) comprises at least one organic solvent selected from the group consisting of benzene, monoalkylated benzene, polyalkylated benzene, an alkyl phosphate, an alkylcyclohexanol ester, a N,N-dialkyl carbonamide, a N-alkyl carbonamide, a N-aryl carbonamide, a N,N-dialkyl carbamate, a tetraalkyl urea, a cycloalkyl urea, a phenylalkyl urea, a N-alkyl-2-pyrrolidone, a N-alkyl caprolactam, and an alcohol.

7. The process of claim 6, wherein the liquid solvent system according to (i) further comprises water, wherein in the liquid solvent system, the molar ratio of organic solvent relative to water is in the range of from 1:1 to 5:1.

8. The process of claim 1, wherein prior to (ii), the process further comprises heating the mixture (A) to a temperature in the range of from 40 to 75° C.

9. The process of claim 1, wherein the providing according to (i) comprises:
   (i.1) preparing a mixture (A.1) comprising at least a portion of the dehydrogenation catalyst and at least a portion of the liquid solvent system;
   (i.2) adding at least a portion of the compound of formula (I) and at least a portion of the compound of formula (II) to the mixture (A.1) prepared in (i.1);
   wherein prior to (i.2), the mixture (A.1) is heated to a temperature in the range of from 40 to 75° C.

10. The process of claim 1, wherein in (ii), the treating of mixture (A) with the oxygen-containing gas is carried out for a period of time in the range of from 0.1 to 240 h, and is carried out by passing the oxygen-containing gas through the mixture (A), and wherein
   the oxygen-containing gas is at least one member selected from the group consisting of oxygen, air, and lean air.

11. The process of claim 1, wherein in (iii), the mixture (B) comprises water and is treated with the oxygen-containing gas after work-up, the work-up comprising separating at least a portion of the water from the mixture (B).

12. The process of claim 1, wherein in (iii), the treating of mixture (B) with the oxygen-containing gas is carried out for a period of time in the range of from 0.1 to 150 h, and is carried out by passing the oxygen-containing gas through the mixture (B), wherein the oxygen-containing gas is at least one member selected from the group consisting of oxygen, air, and lean air.

13. The process of claim 1, wherein the mixture B treated in (iii) comprises an inorganic base selected from the group consisting of potassium hydroxide, sodium hydroxide, and a combination thereof,
   wherein the inorganic base is employed at a molar ratio of the inorganic base relative to compound of formula (I) in the range of from 0.1:1 to 1:1.

14. The process of claim 1, further comprising:
   (iv) separating the compound of formula (IVa), and/or the compound of formula (IVb) from the mixture (C), obtaining a mixture of which at least 95 weight-% consist of the compound of formula (IVa) and/or the compound of formula (IVb);

wherein (iv) comprises (iv.1) extracting the mixture (C);

(iv.2) optionally drying the organic phase obtained from (iv.1), obtaining a solid;

(iv.3) admixing the organic phase obtained from (iv.1) or dissolving the solid obtained from (iv.2) with an organic solvent, at a temperature in the range of from 50 to 150° C., wherein the organic solvent is at least one member selected from the group consisting of benzene, monoalkylated benzene, polyalkylated benzene, an alkyl phosphate, an alkylcyclohexanol ester, a N,N-dialkyl carbonamide, a N-alkyl carbonamide, a N-aryl carbonamide, a N,N-dialkyl carbamate, a tetraalkyl urea, a cycloalkyl urea, a phenylalkyl urea, a N-alkyl-2-pyrrolidone, a N-alkyl caprolactam, and an alcohol having from 1 to 12 carbon atoms;

(iv.4) cooling the solution obtained from (iv.3) to temperature in the range of from −30 to +25° C., obtaining a suspension;

(iv.5) separating the solid from the suspension obtained from (iv.4);

(iv.6) optionally drying the solid obtained from (iv.5), wherein the drying can occur under vacuum;

(iv.7) optionally further purifying the solid obtained from (iv.5) or from (iv.6), wherein the further purifying can occur by chromatography.

15. The process of claim 14, further comprising:

(v) subjecting at least one of the mixture obtained from (iii), the mixture obtained from (iv), and the solid obtained from (iv.6), to a hydrogenation reaction, in the presence of a hydrogenation catalyst, obtaining a mixture comprising a compound of formula (Va)

(Va)

[Chemical structure of anthraquinone with two alkyl chain substituents bearing subscripts n and m]

and/or a compound of formula (Vb)

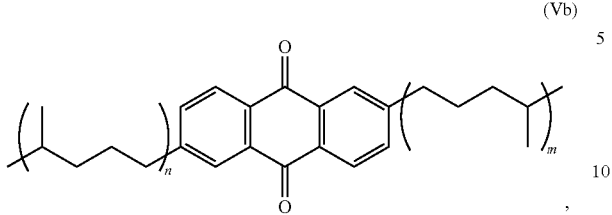
(Vb)

wherein, in each of formula (Va) and formula (Vb), n is 1 or 2 and wherein, in each of formula (Va) and formula (Vb), m is 1 or 2, wherein the hydrogenation reaction according to (v) is carried out in a solvent, wherein the hydrogenation catalyst according to (v) comprises a metal active in hydrogenation;

wherein the hydrogenation reaction according to (v) is carried out at a temperature in the range of from 20 to 200° C.; and wherein the hydrogenation reaction according to (v) is carried out at a hydrogen pressure in the range of from 1 to 50 bar.

16. The process of claim 15, further comprising:

crystallizing the compound of formula (Va) and/or formula (Vb) from the mixture obtained in (v).

17. The process of claim 15, further comprising:

(vi) treating the mixture obtained in (v) with an inorganic base selected from the group consisting of potassium hydroxide, sodium hydroxide, and a combination thereof, obtaining a mixture comprising the compounds of formula (Va) and/or formula (Vb);

wherein the treating according to (vi) is carried out at a temperature in the range of from 30 to 100° C.

18. The process of claim 17, further comprising:

crystallizing the compound of formula (Va) and/or formula (Vb) from the mixture obtained in (vi).

* * * * *

UNITED STATES PATENT AND TRADEMARK OFFICE
CERTIFICATE OF CORRECTION

PATENT NO. : 10,227,281 B2
APPLICATION NO. : 15/315143
DATED : March 12, 2019
INVENTOR(S) : Dominic Riedel et al.

It is certified that error appears in the above-identified patent and that said Letters Patent is hereby corrected as shown below:

In the Specification

Column 7, Line 44, delete "(ii)," and insert --(ii);--.

Column 12, Line 51, delete "solid," and insert --solid;--.

Column 13, Line 34, delete "hydrogenated" and insert --hydrogenated.--.

Column 14, Line 41, delete "Pd" and insert --Pd.--;

Column 14, Line 63, delete "PCy$_3$)," and insert --(PCy$_3$),--.

Column 15, Line 2, delete "PCy$_3$)," and insert --(PCy$_3$),--.

Column 64, Line 58, delete "O$_{26}$H$_{28}$O$_2$" and insert --C$_{26}$H$_{28}$O$_2$--.

Column 66, Line 29, delete "O$_{31}$H$_{36}$O$_2$" and insert --C$_{31}$H$_{36}$O$_2$--;

Column 66, Line 32, delete "O$_{31}$H$_{36}$O$_2$" and insert --C$_{31}$H$_{36}$O$_2$--.

Column 69, Line 3, delete "byproducts" and insert --byproducts.--;

Column 69, Lines 43-44 (approx.), delete "methyl pent" and insert --methylpent--.

Signed and Sealed this
Seventh Day of January, 2020

Andrei Iancu
*Director of the United States Patent and Trademark Office*